US009285378B2

(12) United States Patent
Fuhrmann et al.

(10) Patent No.: US 9,285,378 B2
(45) Date of Patent: Mar. 15, 2016

(54) MEANS AND METHODS FOR DIAGNOSING HEART FAILURE IN A SUBJECT

(75) Inventors: Jens Fuhrmann, Berlin (DE); Regina Reszka, Panketal (DE); Jürgen Kastler, Berlin (DE); Kristina Busch, Berlin (DE); Edgar Leibold, Carlsberg (DE); Hugo Katus, Heidelberg (DE); Norbert Frey, Kronshagen (DE); Johanna Wolf, Mannheim (DE); Tanja Weis, Wiesenbach (DE)

(73) Assignees: Metanomics GmbH, Berlin (DE); Rupreht-Karls-Universität Heidelberg, Heidelberg (DE)

( * ) Notice: Subject to any disclaimer, the term of this patent is extended or adjusted under 35 U.S.C. 154(b) by 0 days.

(21) Appl. No.: 13/574,444

(22) PCT Filed: Jan. 28, 2011

(86) PCT No.: PCT/EP2011/051208
§ 371 (c)(1),
(2), (4) Date: Jul. 20, 2012

(87) PCT Pub. No.: WO2011/092285
PCT Pub. Date: Aug. 4, 2011

(65) Prior Publication Data
US 2012/0286157 A1 Nov. 15, 2012

Related U.S. Application Data

(60) Provisional application No. 61/299,360, filed on Jan. 29, 2010.

(30) Foreign Application Priority Data

Jan. 29, 2010 (EP) .................................... 10000915

(51) Int. Cl.
*G01N 33/92* (2006.01)
*G01N 33/48* (2006.01)

(52) U.S. Cl.
CPC .......... *G01N 33/92* (2013.01); *G01N 2800/325* (2013.01)

(58) Field of Classification Search
CPC .... G01N 2800/325; G01N 33/92; H01J 49/26
USPC ........ 436/63, 71, 127, 128, 161, 173; 435/29; 250/282
See application file for complete search history.

(56) References Cited

U.S. PATENT DOCUMENTS

| 4,540,884 | A | 9/1985 | Stafford et al. |
| 5,397,894 | A | 3/1995 | Wells et al. |
| 6,376,206 | B1 | 4/2002 | Katus et al. |
| 7,588,756 | B1 | 9/2009 | Katus et al. |
| 2005/0103991 | A1 | 5/2005 | Walk et al. |
| 2010/0267062 | A1* | 10/2010 | Frey et al. .................... 435/7.92 |
| 2011/0091929 | A1 | 4/2011 | van Ravenzwaay et al. |
| 2011/0113863 | A1 | 5/2011 | Fuhrmann et al. |
| 2011/0129933 | A1 | 6/2011 | van Ravenzwaay et al. |
| 2011/0163226 | A1 | 7/2011 | van Ravenzwaay et al. |
| 2012/0010094 | A1* | 1/2012 | Spinale et al. .................... 506/9 |
| 2012/0122243 | A1 | 5/2012 | Kamlage et al. |
| 2012/0132797 | A1 | 5/2012 | Strauss et al. |
| 2012/0330558 | A1* | 12/2012 | Baumgartner et al. ......... 702/19 |
| 2013/0023054 | A1* | 1/2013 | Meikle et al. .................... 436/71 |
| 2013/0045217 | A1* | 2/2013 | Laaksonen et al. ........ 424/172.1 |
| 2014/0134654 | A1* | 5/2014 | Rudel et al. .................... 435/11 |

FOREIGN PATENT DOCUMENTS

| DE | 3922873 A1 | 10/1990 |
| DE | 198 15 128 A1 | 10/1998 |
| DE | 199 15 485 A1 | 10/2000 |
| JP | 2006030182 A | 2/2006 |
| WO | WO-03/073464 A1 | 9/2003 |
| WO | 2008118413 A3 | 10/2008 |
| WO | WO-2011/067243 A1 | 6/2011 |
| WO | WO-2011/151252 A2 | 12/2011 |
| WO | WO-2012/000770 A1 | 1/2012 |

OTHER PUBLICATIONS

Christie, W. W., "Rapid Separation and Quantification of Lipid Classes by High Performance Liquid Chromatography and Mass (Light-Scattering) Detection", Journal of Lipid Research, 1985, vol. 26, pp. 507-512.
Ewald, B., et al., "Meta-Analysis of B Type Natriuretic Peptide and N-terminal pro B Natriuretic Peptide in the Diagnosis of Clinical Heart Failure and Population Screening for Left Ventricular Systolic Dysfunction", Internal Medicine Journal, 2008, vol. 38, pp. 101-113.
Fildes, J. E., et al., "Mannose-Binding Lectin Deficiency Offers Protection From Acute Graft Rejection After Heart Transplantation", The Journal of Heart and Lung Transplantation, 2008, vol. 27, No. 12, pp. 1353-1356.
Li, L., et al., "Pravastatin Attenuates Cardiac Dysfunction Induced by Lysophosphatidylcholine in Isolated Rat Hearts", European Journal of Pharmacology, 2010, vol. 640, pp. 139-142.
Masoodi, M., et al., "Lipidomic Analysis of Twenty-Seven Prostanoids and Isoprostanes by Liquid Chromatography/ Electrospray Tandem Mass Spectrometry", Rapid Commun. Mass Spectrom., 2006, vol. 20, pp. 3023-3029.
Niessen, W. M. A., et al., "Liquid Chromatography-Mass Spectrometry General Principles and Instrumentation", Journal of Chromatography A, 1995, vol. 703, pp. 37-57.
Schmidt, H., et al., "LC-MS/MS-Analysis of Sphingosine-1-Phosphate and Related Compounds in Plasma Samples", Prostaglandins & Other Lipid Mediators, 2006, vol. 81, pp. 162-170.
Sedlis, S. P., et al., "Coronary Sinus Lysophosphatidylcholine Accumulation During Rapid Atrial Pacing", The American Journal of Cardiology, 1990, vol. 66, pp. 695-698.

(Continued)

*Primary Examiner* — Maureen Wallenhorst
(74) *Attorney, Agent, or Firm* — Alison R. Scheidler

(57) ABSTRACT

The present invention relates to the field of diagnostic methods. Specifically, the present invention contemplates a method for diagnosing heart failure in a subject, a method for identifying whether a subject is in need for a therapy of heart failure or a method for determining whether a heart failure therapy is successful. The invention also relates to tools for carrying out the aforementioned methods, such as diagnostic devices.

14 Claims, No Drawings

(56) References Cited

OTHER PUBLICATIONS

Troelsen, L. N., et al., "Mortality and Predictors of Mortality in Rheumatoid Arthritis—A Role for Mannose-binding Lectin?", Journal of Rheumatology, 2010, vol. 37, No. 3, pp. 536-543.

Ueland, T., et al., "Mannose Binding Lectin and Soluble Toll-Like Receptor 2 in Heart Failure Following Acute Myocardial Infarction", Journal of Cardiac Failure, 2006, vol. 12, No. 8, pp. 659-663.

Yamada, H., et al., "Dansyl Chloride Derivatization of Methamphetamine: A Method with Advantages for Screening and Analysis of Methamphetamine in Urine", Journal of Analytical Toxicology, 2002, vol. 26, pp. 17-22.

International Preliminary Report on Patentability for PCT/EP2011/051208 mailed Jul. 31, 2012.

International Search Report for PCT/EP2011/051208 mailed Sep. 14, 2011.

\* cited by examiner

MEANS AND METHODS FOR DIAGNOSING HEART FAILURE IN A SUBJECT

RELATED APPLICATIONS

This application is a national stage application (under 35 U.S.C. §371) of PCT/EP2011/051208, filed Jan. 28, 2011, which claims benefit of U.S. Provisional Application No. 61/299,360, filed Jan. 29, 2010, and European Application No. 10000915.8, filed Jan. 29, 2010.

The present invention relates to the field of diagnostic methods. Specifically, the present invention contemplates a method for diagnosing heart failure in a subject, a method for identifying whether a subject is in need for a therapy of heart failure or a method for determining whether a heart failure therapy is successful. The invention also relates to tools for carrying out the aforementioned methods, such as diagnostic devices.

Heart failure is a severe problem in modern medicine. The impaired function of the heart can give rise to life-threatening conditions and results in discomfort for the patients suffering from heart failure. Heart failure can affect the right or the left heart, respectively, and can vary in strength. A classification system was originally developed by the New York Heart association (NYHA). According to the classification system, the mild cases of heart failure are categorized as class I cases. These patients only show symptoms under extreme exercise. The intermediate cases show more pronounced symptoms already under less exercise (classes II and III) while class IV, shows already symptoms at rest (New York Heart Association. Diseases of the heart and blood vessels. Nomenclature and criteria for diagnosis, 6$^{th}$ ed. Boston: Little, Brown and co, 1964; 114).

The prevalence of heart failure steadily increases in the population of the western developed countries over the last years. One reason for said increase can be seen in an increased average life expectation due to modern medicine. The mortality rate caused by heart failure, however, could be further reduced by improved diagnostic and therapeutic approaches. The so-called "Framingham" study reported a reduction of the 5 year mortality from 70% to 59% in men and from 57% to 45% in women when comparing a time window of 1950 to 1969 with 1990 to 1999. The "Mayo" study shows a reduction from 65% to 50% for men for a time window of 1996 to 2000 compared to 1979 to 1984 and from 51% to 46% for women. Notwithstanding this reduction of the mortality rate, the overall mortality due to heart failure is still a major burden to societies. One-year mortality for NYHA class II to III patients under ACE inhibitor therapy is still between 9-12% (SOLVED) and for NYHA class IV without ACE inhibitor therapy 52% (Consensus).

Diagnostic techniques such as echocardiography are dependent on the experience of the individual investigator and, thus, not always reliable. Moreover, these techniques sometimes fail to diagnose the early onset of heart failure. Biochemical assays which are based on cardiac hormones such as Brain natriuretic peptides (BNP) are also influenced by other diseases and disorders such as renal insufficiency or depend on the overall physical condition of the patient. Nevertheless, Brain natriuretic peptides are the current gold standard for biochemically assessing heart failure. According to a recent study comparing BNP and N-terminal pro-BNP (NT-proBNP) in the diagnosis of heart failure, BNP is a better indicator for heart failure and left ventricular systolic dysfunction than NT-proBNP. In groups of symptomatic patients, a diagnostic odds ratio of 27 for BNP compares with a sensitivity of 85% and specificity of 84% in detecting heart failure (Ewald 2008, Intern Med J 38 (2):101-13.).

However, it is a goal of modern medicine to reliably identify and treat patients with heart failure and, in particular, to identify them at the early onset of heart failure, i.e. at the early NYHA stages I to III and in particular at NYHA stage I. Accordingly, means and methods for reliably diagnosing heart failure are highly desired but not yet available.

Therefore, the present invention pertains to a method for diagnosing heart failure in a subject comprising the steps of:
a) determining in a sample of a subject suspected to suffer from heart failure the amount of at least one biomarker selected from the biomarkers listed in Table 1a to c, 3, 4a to c or 6;
b) comparing the amount of the said at least one biomarker to a reference, whereby heart failure is to be diagnosed.

The method as referred to in accordance with the present invention includes a method which essentially consists of the aforementioned steps or a method which includes further steps. However, it is to be understood that the method, in a preferred embodiment, is a method carried out ex vivo, i.e. not practised on the human or animal body. The method, preferably, can be assisted by automation.

The term "diagnosing" as used herein refers to assessing whether a subject suffers from the heart failure, or not. As will be understood by those skilled in the art, such an assessment, although preferred to be, may usually not be correct for 100% of the investigated subjects. The term, however, requires that a statistically significant portion of subjects can be correctly assessed and, thus, diagnosed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% or at least 95%. The p-values are, preferably, 0.2, 0.1, or 0.05.

The term includes individual diagnosis of heart failure or its symptoms as well as continuous monitoring of a patient. Monitoring, i.e. diagnosing the presence or absence of heart failure or the symptoms accompanying it at various time points, includes monitoring of patients known to suffer from heart failure as well as monitoring of subjects known to be at risk of developing heart failure. Furthermore, monitoring can also be used to determine whether a patient is treated successfully or whether at least symptoms of heart failure can be ameliorated over time by a certain therapy. Moreover, the term also includes classifying a subject according to the New York Heart Association (NYHA) classes for heart failure. According to this classification, heart failure can be subdivided into four classes. Subjects exhibiting class I show no limitation in activities except under strong physical exercise. Subjects exhibiting class II show slight, mild limitation of activity, while comfortable at rest or under mild exertion. Subjects exhibiting class III show marked limitation of any activity, while comfortable only at rest. Subjects exhibiting class IV show discomfort and symptoms even at rest. Preferably, heart failure to be determined in accordance with the present invention is mild heart failure, i.e. heart failure according to NYHA class I, or intermediated heart failure, i.e. heart failure according to NYHA class II and/or III. Preferably, said heart failure is heart failure according to NYHA class I and the said at least one biomarker is selected from Table 4a to c or 6. Also preferably, said heart failure is heart failure according to NYHA class II or III and the at least one biomarker is selected from Table 1a to c or 3.

Another staging system is provided by the American Heart Association. Four stages of heart failure are subdivided: Stage A: Patients at high risk for developing HF in the future but no functional or structural heart disorder. Stage B: a structural heart disorder but no symptoms at any stage. Stage C: previous or current symptoms of heart failure in the context of an underlying structural heart problem, but managed with medical treatment. Stage D: advanced disease requiring hospital-based support, a heart transplant or palliative care. It will be understood that the method of the present invention can also be used for staging heart failure according to this system, preferably, the identified biomarkers shall allow to diagnose heart failure according to stages A to C and to discriminate between the mild stage A (Table 4a to c or 6) and the more severe stages B and C (Table 1a to c or 3).

The term "heart failure" as used herein relates to an impaired function of the heart. The said impairment can be a systolic dysfunction resulting in a significantly reduced ejection fraction of blood from the heart and, thus, a reduced blood flow. Specifically, systolic heart failure is characterized by a significantly reduced left ventricular ejection fraction (LEVF), preferably, an ejection fraction of less than 55%. Alternatively, the impairment can be a diastolic dysfunction, i.e. a failure of the ventricle to properly relax. The latter is usually accompanied by a stiffer ventricular wall. The diastolic dysfunction causes inadequate filling of the ventricle and, therefore, results in consequences for the blood flow, in general. Thus, diastolic dysfunction also results in elevated end-diastolic pressures, and the end result is comparable to the case of systolic dysfunction (pulmonary edema in left heart failure, peripheral edema in right heart failure.) Heart failure may, thus, affect the right heart (pulmonary circulation), the left heart (body circulation) or both. Techniques for measuring an impaired heart function and, thus, heart failure, are well known in the art and include echocardiography, electrophysiology, angiography, and the determination of peptide biomarkers, such as the Brain Natriuretic Peptide (BNP) or the N-terminal fragment of its propeptide, in the blood. It will be understood that the impaired function of the heart can occur permanently or only under certain stress or exercise conditions. Dependent on the strength of the symptoms, heart failure can be classified as set forth elsewhere herein. Typical symptoms of heart failure include dyspnea, chest pain, dizziness, confusion, pulmonary and/or peripheral edema. It will be understood that the occurrence of the symptoms as well as their severity may depended on the severity of heart failure and the characteristics and causes of the heart failure, systolic or diastolic or restrictive i.e. right or left heart located heart failure. Further symptoms of heart failure are well known in the art and are described in the standard text books of medicine, such as Stedman or Brunnwald.

Preferably, heart failure as used herein relates to congestive heart failure and, more preferably, the subject exhibiting said heart failure suffers from a dilatative cardiomyopathy. Also more preferably, the subject in accordance with the present invention suffers from ischemic cardiomyopathy or hypertrophic cardiomyopathy. In another embodiment the subject in accordance with the present invention suffers from dilatative cardiomyopathy and ischemic cardiomyopathy or from dilatative cardiomyopathy and hypertrophic cardiomyopathy. However, heart failure as referred to in accordance with the present invention also includes ischemic heart failure, myocardial hypertrophy, valvular heart disease, restrictive cardiomyopathy, constrictive pericardial disorders, and hypertensive disease.

The term "biomarker" as used herein refers to a molecular species which serves as an indicator for a disease or effect as referred to in this specification. Said molecular species can be a metabolite itself which is found in a sample of a subject. Moreover, the biomarker may also be a molecular species which is derived from said metabolite. In such a case, the actual metabolite will be chemically modified in the sample or during the determination process and, as a result of said modification, a chemically different molecular species, i.e. the analyte, will be the determined molecular species. It is to be understood that in such a case, the analyte represents the actual metabolite and has the same potential as an indicator for the respective medical condition.

In the method according to the present invention, at least one metabolite of the aforementioned group of biomarkers, i.e. the biomarkers as shown in Tables 1a to c, 3, 4a to c and/or 6, is to be determined. However, more preferably, a group of biomarkers will be determined in order to strengthen specificity and/or sensitivity of the assessment. Such a group, preferably, comprises at least 2, at least 3, at least 4, at least 5, at least 10 or up to all of the said biomarkers shown in the Tables. In addition to the specific biomarkers recited in the specification, other biomarkers may be, preferably, determined as well in the methods of the present invention.

A metabolite as used herein refers to at least one molecule of a specific metabolite up to a plurality of molecules of the said specific metabolite. It is to be understood further that a group of metabolites means a plurality of chemically different molecules wherein for each metabolite at least one molecule up to a plurality of molecules may be present. A metabolite in accordance with the present invention encompasses all classes of organic or inorganic chemical compounds including those being comprised by biological material such as organisms. Preferably, the metabolite in accordance with the present invention is a small molecule compound. More preferably, in case a plurality of metabolites is envisaged, said plurality of metabolites representing a metabolome, i.e. the collection of metabolites being comprised by an organism, an organ, a tissue, a body fluid or a cell at a specific time and under specific conditions.

The metabolites are small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including eg. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000 Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da.

The term "sample" as used herein refers to samples from body fluids, preferably, blood, plasma, serum, saliva or urine, or samples derived, e.g., by biopsy, from cells, tissues or organs, in particular from the heart. More preferably, the sample is a blood, plasma or serum sample, most preferably, a plasma sample. Biological samples can be derived from a subject as specified elsewhere herein. Techniques for obtaining the aforementioned different types of biological samples are well known in the art. For example, blood samples may be obtained by blood taking while tissue or organ samples are to be obtained, e.g., by biopsy.

The aforementioned samples are, preferably, pre-treated before they are used for the method of the present invention. As described in more detail below, said pre-treatment may include treatments required to release or separate the compounds or to remove excessive material or waste. Suitable techniques comprise centrifugation, extraction, fractioning, ultrafiltration, protein precipitation followed by filtration and purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pre-treatments depend on the means used for carrying out the method of the invention and are well known to the person skilled in the art. Pre-treated samples as described before are also comprised by the term "sample" as used in accordance with the present invention.

The term "subject" as used herein relates to animals and, preferably, to mammals. More preferably, the subject is a primate and, most preferably, a human. The subject, preferably, is suspected to suffer from heart failure, i.e. it may already show some or all of the symptoms associated with the disease. More preferably, it exhibits symptoms according to any one of NYHA classes I to III. Moreover, the subject shall also preferably exhibit congestive systolic heart failure due to contractile dysfunction such as dilated cardiomyopathy. Preferably, the subject, however, is besides the aforementioned diseases and disorders apparently healthy. In particular, it shall, preferably, not exhibit symptoms according to NYHA class IV patients or suffer from stroke, myocardial infarction within the last 4 month before the sample has been taken or from acute or chronic inflammatory diseases and malignant tumors. Furthermore, the subject is preferably in stable medications within the last 4 weeks before the sample was taken.

The term "determining the amount" as used herein refers to determining at least one characteristic feature of a biomarker to be determined by the method of the present invention in the sample. Characteristic features in accordance with the present invention are features which characterize the physical and/or chemical properties including biochemical properties of a biomarker. Such properties include, e.g., molecular weight, viscosity, density, electrical charge, spin, optical activity, colour, fluorescence, chemoluminescence, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a biomarker by standard operations, e.g., mathematical calculations such as multiplication, division or logarithmic calculus. Most preferably, the at least one characteristic feature allows the determination and/or chemical identification of the said at least one biomarker and its amount. Accordingly, the characteristic value, preferably, also comprises information relating to the abundance of the biomarker from which the characteristic value is derived. For example, a characteristic value of a biomarker may be a peak in a mass spectrum. Such a peak contains characteristic information of the biomarker, i.e. the m/z information, as well as an intensity value being related to the abundance of the said biomarker (i.e. its amount) in the sample.

As discussed before, each biomarker comprised by a sample may be, preferably, determined in accordance with the present invention quantitatively or semi-quantitatively. For quantitative determination, either the absolute or precise amount of the biomarker will be determined or the relative amount of the biomarker will be determined based on the value determined for the characteristic feature(s) referred to herein above. The relative amount may be determined in a case were the precise amount of a biomarker can or shall not be determined. In said case, it can be determined whether the amount in which the biomarker is present is enlarged or diminished with respect to a second sample comprising said biomarker in a second amount. In a preferred embodiment said second sample comprising said biomarker shall be a calculated reference as specified elsewhere herein. Quantitatively analysing a biomarker, thus, also includes what is sometimes referred to as semi-quantitative analysis of a biomarker.

Moreover, determining as used in the method of the present invention, preferably, includes using a compound separation step prior to the analysis step referred to before. Preferably, said compound separation step yields a time resolved separation of the metabolites comprised by the sample. Suitable techniques for separation to be used preferably in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. Most preferably, LC and/or GC are chromatographic techniques to be envisaged by the method of the present invention. Suitable devices for such determination of biomarkers are well known in the art. Preferably, mass spectrometry is used in particular gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). Most preferably, LC-MS and/or GC-MS are used as described in detail below. Said techniques are disclosed in, e.g., Nissen 1995, Journal of Chromatography A, 703: 37-57, U.S. Pat. No. 4,540,884 or U.S. Pat. No. 5,397,894, the disclosure content of which is hereby incorporated by reference. As an alternative or in addition to mass spectrometry techniques, the following techniques may be used for compound determination: nuclear magnetic resonance (NMR), magnetic resonance imaging (MRI), Fourier transform infrared analysis (FT-IR), ultraviolet (UV) spectroscopy, refraction index (RI), fluorescent detection, radiochemical detection, electrochemical detection, light scattering (LS), dispersive Raman spectroscopy or flame ionisation detection (FID). These techniques are well known to the person skilled in the art and can be applied without further ado. The method of the present invention shall be, preferably, assisted by automation. For example, sample processing or pre-treatment can be automated by robotics. Data processing and comparison is, preferably, assisted by suitable computer programs and databases. Automation as described herein before allows using the method of the present invention in high-throughput approaches.

Moreover, the at least one biomarker can also be determined by a specific chemical or biological assay. Said assay shall comprise means which allow to specifically detect the at least one biomarker in the sample. Preferably, said means are capable of specifically recognizing the chemical structure of the biomarker or are capable of specifically identifying the biomarker based on its capability to react with other compounds or its capability to elicit a response in a biological read out system (e.g., induction of a reporter gene). Means which are capable of specifically recognizing the chemical structure of a biomarker are, preferably, antibodies or other proteins which specifically interact with chemical structures, such as receptors or enzymes. Specific antibodies, for instance, may be obtained using the biomarker as antigen by methods well known in the art. Antibodies as referred to herein include both polyclonal and monoclonal antibodies, as well as fragments thereof, such as Fv, Fab and F(ab)$_2$ fragments that are capable of binding the antigen or hapten. The present invention also includes humanized hybrid antibodies wherein amino acid sequences of a non-human donor antibody exhibiting a desired antigen-specificity are combined with sequences of a human acceptor antibody. Moreover, encompassed are single chain antibodies. The donor sequences will usually include at least the antigen-binding amino acid residues of the donor but may comprise other structurally and/or functionally relevant amino acid residues of the donor antibody as well. Such hybrids can be prepared by several methods well known in the art. Suitable proteins which are capable of specifically recognizing the biomarker are, preferably, enzymes which are involved in the metabolic conversion of the said biomarker. Said enzymes may either use the biomarker as a substrate or may convert a substrate into the biomarker. Moreover, said antibodies may be used as a basis to generate oligopeptides which specifically recognize the biomarker. These oligopeptides shall, for example, comprise the enzyme's binding domains or pockets for the said biomarker. Suitable antibody and/or enzyme based assays may be RIA (radioimmunoassay), ELISA (enzyme-linked immunosorbent assay), sandwich enzyme immune tests, electro-chemiluminescence sandwich immunoassays (ECLIA), dissociation-enhanced lanthanide fluoro immuno assay (DELFIA) or solid phase immune tests. Moreover, the biomarker may also be determined based on its capability to react with other compounds, i.e. by a specific chemical reaction. Further, the biomarker may be determined in a sample due to its capability to elicit a response in a biological read out system. The biological response shall be detected as read out indicating the presence and/or the amount of the biomarker comprised by the sample. The biological response may be, e.g., the induction of gene expression or a phenotypic response of a cell or an organism. In a preferred embodiment the determination of the least one biomarker is a quantitative process, e.g., allowing also the determination of the amount of the at least one biomarker in the sample.

As described above, said determining of the at least one biomarker can, preferably, comprise mass spectrometry (MS). Mass spectrometry as used herein encompasses all techniques which allow for the determination of the molecular weight (i.e. the mass) or a mass variable corresponding to a compound, i.e. a biomarker, to be determined in accordance with the present invention. Preferably, mass spectrometry as used herein relates to GC-MS, LC-MS, direct infusion mass spectrometry, FT-ICR-MS, CE-MS, HPLC-MS, quadrupole mass spectrometry, any sequentially coupled mass spectrometry such as MS-MS or MS-MS-MS, ICP-MS, Py-MS, TOF or any combined approaches using the aforementioned techniques. How to apply these techniques is well known to the person skilled in the art. Moreover, suitable devices are commercially available. More preferably, mass spectrometry as used herein relates to LC-MS and/or GC-MS, i.e. to mass spectrometry being operatively linked to a prior chromatographic separation step. More preferably, mass spectrometry as used herein encompasses quadrupole MS. Most preferably, said quadrupole MS is carried out as follows: a) selection of a mass/charge quotient (m/z) of an ion created by ionisation in a first analytical quadrupole of the mass spectrometer, b) fragmentation of the ion selected in step a) by applying an acceleration voltage in an additional subsequent quadrupole which is filled with a collision gas and acts as a collision chamber, c) selection of a mass/charge quotient of an ion created by the fragmentation process in step b) in an additional subsequent quadrupole, whereby steps a) to c) of the method are carried out at least once and analysis of the mass/charge quotient of all the ions present in the mixture of substances as a result of the ionisation process, whereby the quadrupole is filled with collision gas but no acceleration voltage is applied during the analysis. Details on said most preferred mass spectrometry to be used in accordance with the present invention can be found in WO 03/073464.

More preferably, said mass spectrometry is liquid chromatography (LC) MS and/or gas chromatography (GC) MS. Liquid chromatography as used herein refers to all techniques which allow for separation of compounds (i.e. metabolites) in liquid or supercritical phase. Liquid chromatography is characterized in that compounds in a mobile phase are passed through the stationary phase. When compounds pass through the stationary phase at different rates they become separated in time since each individual compound has its specific retention time (i.e. the time which is required by the compound to pass through the system). Liquid chromatography as used herein also includes HPLC. Devices for liquid chromatography are commercially available, e.g. from Agilent Technologies, USA. Gas chromatography as applied in accordance with the present invention, in principle, operates comparable to liquid chromatography. However, rather than having the compounds (i.e. metabolites) in a liquid mobile phase which is passed through the stationary phase, the compounds will be present in a gaseous volume. The compounds pass the column which may contain solid support materials as stationary phase or the walls of which may serve as or are coated with the stationary phase. Again, each compound has a specific time which is required for passing through the column. Moreover, in the case of gas chromatography it is preferably envisaged that the compounds are derivatised prior to gas chromatography. Suitable techniques for derivatisation are well known in the art. Preferably, derivatisation in accordance with the present invention relates to methoxymation and trimethylsilylation of, preferably, polar compounds and transmethylation, methoxymation and trimethylsilylation of, preferably, non-polar (i.e. lipophilic) compounds, The term "reference" refers to values of characteristic features of each of the biomarker which can be correlated to a medical condition, i.e. the presence or absence of the disease, diseases status or an effect referred to herein. Preferably, a reference is a threshold value (e.g., an amount or ratio of amounts) for a biomarker whereby values found in a sample to be investigated which are higher than or essentially identical to the threshold are indicative for the presence of a medical condition while those being lower are indicative for the absence of the medical condition. It will be understood that also preferably, a reference may be a threshold value for a biomarker whereby values found in a sample to be investigated which are lower or identical than the threshold are indicative for the presence of a medical condition while those being higher are indicative for the absence of the medical condition.

In accordance with the aforementioned method of the present invention, a reference is, preferably, a reference obtained from a sample from a subject or group of subjects known to suffer from heart failure. In such a case, a value for the at least one biomarker found in the test sample being essentially identical is indicative for the presence of the disease. Moreover, the reference, also preferably, could be from a subject or group of subjects known not to suffer from heart failure, preferably, an apparently healthy subject. In such a case, a value for the at least one biomarker found in the test sample being altered with respect to the reference is indicative for the presence of the disease. The same applies mutatis mutandis for a calculated reference, most preferably the average or median, for the relative or absolute value of the at least one biomarker of a population of individuals comprising the subject to be investigated. The absolute or relative values of the at least one biomarker of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 or 10,000 subjects. It is to be understood that the subject to be diagnosed by the method of the present invention and the subjects of the said plurality of subjects are of the same species.

The value for the at least one biomarker of the test sample and the reference values are essentially identical, if the values for the characteristic features and, in the case of quantitative determination, the intensity values are essentially identical. Essentially identical means that the difference between two values is, preferably, not significant and shall be characterized in that the values for the intensity are within at least the interval between 1st and $99^{th}$ percentile, $5^{th}$ and $95^{th}$ percentile, $10^{th}$ and $90^{th}$ percentile, $20^{th}$ and $80^{th}$ percentile, $30^{th}$ and $70^{th}$ percentile, $40^{th}$ and $60^{th}$ percentile of the reference value, preferably, the $50^{th}$, $60^{th}$, $70^{th}$, $80^{th}$, $90^{th}$ or $95^{th}$ percentile of the reference value. Statistical test for determining whether two amounts are essentially identical are well known in the art and are also described elsewhere herein.

An observed difference for two values, on the other hand, shall be statistically significant. A difference in the relative or absolute value is, preferably, significant outside of the interval between $45^{th}$ and $55^{th}$ percentile, $40^{th}$ and $60^{th}$ percentile, $30^{th}$ and $70^{th}$ percentile, $20^{th}$ and $80^{th}$ percentile, $10^{th}$ and $90^{th}$ percentile, $5^{th}$ and $95^{th}$ percentile, 1st and $99^{th}$ percentile of the reference value. Preferred changes and ratios of the medians are described in the accompanying Tables as well as in the Examples.

Preferably, the reference, i.e. values for at least one characteristic feature of the at least one biomarker or ratios thereof, will be stored in a suitable data storage medium such as a database and are, thus, also available for future assessments.

The term "comparing" refers to determining whether the determined value of a biomarker is essentially identical to a reference or differs therefrom. Preferably, a value for a biomarker is deemed to differ from a reference if the observed difference is statistically significant which can be determined by statistical techniques referred to elsewhere in this description. If the difference is not statistically significant, the biomarker value and the reference are essentially identical. Based on the comparison referred to above, a subject can be assessed to suffer from the disease, or not.

For the specific biomarkers referred to in this specification, preferred values for the changes in the relative amounts or ratios (i.e. the changes expressed as the ratios of the medians) or the kind of regulation (i.e. "up"- or "down"-regulation resulting in a higher or lower relative and/or absolute amount or ratio) are indicated in the Tables and in the Examples below. The median of ratios indicates the degree of increase or decrease, e.g., a value of 2 means that the amount is twice the amount of the biomarker compared to the reference. Moreover, it is apparent whether there is an "up-regulation" or a "down-regulation". In the case of an "up-regulation" the ratio of median shall exceed 1.0 while it will be below 1.0 in case of a "down"-regulation. Accordingly, the direction of regulation can be derived from the Tables as well.

The comparison is, preferably, assisted by automation. For example, a suitable computer program comprising algorithms for the comparison of two different data sets (e.g., data sets comprising the values of the characteristic feature(s)) may be used. Such computer programs and algorithms are well known in the art. Notwithstanding the above, a comparison can also be carried out manually.

Advantageously, it has been found in the study underlying the present invention that the amounts of the specific biomarkers referred to above are indicators for heart failure. Accordingly, the at least one biomarker as specified above in a sample can, in principle, be used for assessing whether a subject suffers from heart failure. This is particularly helpful for an efficient diagnosis of the disease as well as for improving of the pre-clinical and clinical management of heart failure as well as an efficient monitoring of patients. Moreover, the findings underlying the present invention will also facilitate the development of efficient drug-based therapies or other interventions including nutritional diets against heart failure as set forth in detail below.

In a preferred embodiment of the method of the present invention, said sample of the subject has been obtained at rest and said at least one biomarker is selected from Table 1a to c or 4a to c.

In a further preferred embodiment of the method of the present invention, said sample of the subject has been obtained under exercise and said at least one biomarker is selected from Table 3 or 6.

The term "exercise" as used herein refers to applying load of work to the subject. Preferably, the said work load is a permanent work load. Applying such a permanent work load can be achieved by spiroergometry as described in the accompanying Examples below, in detail. Preferably, the load of work applied to the subject is constantly increased. A preferred way for exercise is described in the accompanying Examples, below. The sample of the subject to be investigated by the method of the present invention is, preferably, obtained at the peak of exercise (see also Examples, below). In another preferred embodiment of the method of the present invention, said heart failure is dilated cardiomyopathy and the at least one biomarker is selected from Table 1a or 4a.

In yet another preferred embodiment of the method of the present invention, said heart failure is ischemic cardiomyopathy and/or dilatative cardiomyopathy and the at least one biomarker is selected from Table 1b or 4b.

In another preferred embodiment of the method of the present invention, said heart failure is hypertrophic cardiomyopathy and/or dilatative cardiomyopathy and the at least one biomarker is selected from Table 1c or 4c.

The definitions and explanations of the terms made above apply mutatis mutandis for the following embodiments of the present invention except specified otherwise herein below.

The present invention also contemplates a method for diagnosing heart failure in a subject comprising the steps of:
a) determining in a first and a second sample of a subject suspected to suffer from heart failure the amount of at least one biomarker selected from the biomarkers listed in Table 2 or 5, wherein said first sample has been obtained at rest and said second sample has been obtained under exercise;
b) calculating a ration of the amount of the at least one biomarker determined in the first and the second sample; and
c) comparing the calculated ratio to a reference, whereby heart failure is to be diagnosed.

The term "calculating" as used herein refers to calculating the ration of the amount of the at least one biomarker determined in the second sample (t1) and the amount of the at least one biomarker determined in the first sample (t0), i.e. t1/t0. It will be understood that the term calculating also encompasses other mathematical operations which result in a parameter which is correlated to the said ratio.

It will be understood that a reference in case of the aforementioned method of the present invention shall be a reference ratio, i.e. preferably a ratio (t1/t0) derived from either a subject or group of subjects known to suffer not from heart failure or a subject or group of subjects known to suffer from heart failure. An essential difference in the ratio in the first case indicates the presence heart failure while an essential difference in the second case, preferably, indicates the absence of heart failure. Likewise, essentially identical ratios in the first case (i.e. the comparison to a reference ratio from a healthy subject) indicates the absence of heart failure while in the second case, an essentially identical ratio indicates the presence of heart failure. In addition, the further explanations and definitions made for references above, apply accordingly.

In a preferred embodiment of the aforementioned method of the present invention, said heart failure is mild to moderate heart failure according to NYHA class I and the said at least one biomarker is selected from Table 5.

The present invention also relates to a method for identifying whether a subject is in need for a therapy of heart failure or a change of therapy comprising the steps of the methods of the present invention and the further step of identifying a subject in need if heart failure is diagnosed.

The phrase "in need for a therapy of heart failure" as used herein means that the disease in the subject is in a status where therapeutic intervention is necessary or beneficial in order to ameliorate or treat heart failure or the symptoms associated therewith. Accordingly, the findings of the studies underlying the present invention do not only allow diagnosing heart failure in a subject but also allow for identifying subjects which should be treated by an heart failure therapy or whose heart failure therapy needs adjustment. Once the subject has been identified, the method may further include a step of making recommendations for a therapy of heart failure.

A therapy of heart failure as used in accordance with the present invention, preferably, relates to a therapy which comprises or consists of the administration of at least one drug selected from the group consisting of: ACE Inhibitors (ACEI), Beta Blockers, AT1-Inhibitors, Aldosteron Antagonists, Renin Antagonists, Diuretics, Ca-Sensitizer, Digitalis Glykosides, polypeptides of the protein S100 family (as disclosed by DE000003922873A1, DE000019815128A1 or DE000019915485A1 hereby incorporated by reference), natriuretic peptides such as BNP (Nesiritide (human recombinant Brain Natriuretic Peptide-BNP)) or ANP.

The present invention further relates to a method for determining whether a therapy against heart failure is successful in a subject comprising the steps of the methods of the present invention and the further step of determining whether a therapy is successful if no heart failure is diagnosed.

It is to be understood that a heart failure therapy will be successful if heart failure or at least some symptoms thereof can be treated or ameliorated compared to an untreated subject. Moreover, a therapy is also successful as meant herein if the disease progression can be prevented or at least slowed down compared to an untreated subject.

The aforementioned methods for the determination of the at least one biomarker can be implemented into a device. A device as used herein shall comprise at least the aforementioned means. Moreover, the device, preferably, further comprises means for comparison and evaluation of the detected characteristic feature(s) of the at least one biomarker and, also preferably, the determined signal intensity. The means of the device are, preferably, operatively linked to each other. How to link the means in an operating manner will depend on the type of means included into the device. For example, where means for automatically qualitatively or quantitatively determining the biomarker are applied, the data obtained by said automatically operating means can be processed by, e.g., a computer program in order to facilitate the assessment. Preferably, the means are comprised by a single device in such a case. Said device may accordingly include an analyzing unit for the biomarker and a computer unit for processing the resulting data for the assessment. Preferred devices are those which can be applied without the particular knowledge of a specialized clinician, e.g., electronic devices which merely require loading with a sample.

Alternatively, the methods for the determination of the at least one biomarker can be implemented into a system comprising several devices which are, preferably, operatively linked to each other. Specifically, the means must be linked in a manner as to allow carrying out the method of the present invention as described in detail above. Therefore, operatively linked, as used herein, preferably, means functionally linked. Depending on the means to be used for the system of the present invention, said means may be functionally linked by connecting each mean with the other by means which allow data transport in between said means, e.g., glass fiber cables, and other cables for high throughput data transport. Nevertheless, wireless data transfer between the means is also envisaged by the present invention, e.g., via LAN (Wireless LAN, W-LAN). A preferred system comprises means for determining biomarkers. Means for determining biomarkers as used herein encompass means for separating biomarkers, such as chromatographic devices, and means for metabolite determination, such as mass spectrometry devices. Suitable devices have been described in detail above. Preferred means for compound separation to be used in the system of the present invention include chromatographic devices, more preferably devices for liquid chromatography, HPLC, and/or gas chromatography. Preferred devices for compound determination comprise mass spectrometry devices, more preferably, GC-MS, LC-MS, direct infusion mass spectrometry, FT-ICR-MS, CE-MS, HPLC-MS, quadrupole mass spectrometry, sequentially coupled mass spectrometry (including MS-MS or MS-MS-MS), ICP-MS, Py-MS or TOF. The separation and determination means are, preferably, coupled to each other. Most preferably, LC-MS and/or GC-MS are used in the system of the present invention as described in detail elsewhere in the specification. Further comprised shall be means for comparing and/or analyzing the results obtained from the means for determination of biomarkers. The means for comparing and/or analyzing the results may comprise at least one databases and an implemented computer program for comparison of the results. Preferred embodiments of the aforementioned systems and devices are also described in detail below.

Therefore, the present invention relates to a diagnostic device comprising:
  a) an analysing unit comprising a detector for at least one biomarker as listed in any one of Tables 1a to c, 3, 4a to c or 6, wherein said analyzing unit is adapted for determining the amount of the said biomarker detected by the detector, and, operatively linked thereto;
  b) an evaluation unit comprising a computer comprising tangibly embedded a computer program code for carrying out a comparison of the determined amount of the at least one biomarker and a reference amount and a data base comprising said reference amount as for the said biomarker whereby it will be diagnosed whether a subject suffers from heart failure, is in need for a therapy of heart failure or has underwent a successful therapy of heart failure if the result of the comparison for the at least one biomarker is essentially identical to the kind of regulation and/or fold of regulation indicated for the respective at least one biomarker in any one of Tables 1a to c, 3, 4a to c or 6.

In a preferred embodiment, the device comprises a further database comprising the kind of regulation and/or fold of regulation values indicated for the respective at least one biomarker in any one of Tables 1a to c, 3, 4a to c or 6 and a further tangibly embedded computer program code for carrying out a comparison between the determined kind of regulation and/or fold of regulation values and those comprised by the database.

Therefore, the present invention also relates to a diagnostic device comprising:
  a) an analysing unit comprising a detector for at least one biomarker as listed in any one of Tables 2 or 5, wherein said analyzing unit is adapted for determining the amount of the said biomarker detected by the detector, and, operatively linked thereto;
  b) an evaluation unit comprising a computer comprising tangibly embedded a computer program code for (i) calculating a ratio of the at least one biomarker of a second and a first sample and (ii) carrying out a comparison of the determined ratio of the at least one biomarker and a reference ratio and a data base comprising said reference ratio for the said biomarker whereby it will be diagnosed whether a subject suffers from heart failure, is in need for a therapy of heart failure or has underwent a successful therapy of heart failure if the result of the comparison for the at least one biomarker is essentially identical to the kind of regulation and/or fold of regulation indicated for the respective at least one biomarker in any one of Tables 2 or 5.

In a preferred embodiment, the device comprises a further database comprising the kind of regulation and/or fold of regulation values indicated for the respective at least one biomarker in any one of Tables 2 or 5 and a further tangibly embedded computer program code for carrying out a comparison between the determined kind of regulation and/or fold of regulation values and those comprised by the database.

Furthermore, the present invention relates to a data collection comprising characteristic values of at least one biomarker being indicative for a medical condition or effect as set forth above (i.e. diagnosing heart failure in a subject, identifying whether a subject is in need for a therapy of heart failure or determining whether a heart failure therapy is successful).

The term "data collection" refers to a collection of data which may be physically and/or logically grouped together. Accordingly, the data collection may be implemented in a single data storage medium or in physically separated data storage media being operatively linked to each other. Preferably, the data collection is implemented by means of a database. Thus, a database as used herein comprises the data collection on a suitable storage medium. Moreover, the database, preferably, further comprises a database management system. The database management system is, preferably, a network-based, hierarchical or object-oriented database management system. Furthermore, the database may be a federal or integrated database. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative for a medical condition or effect as set forth above (e.g. a query search). Thus, if an identical or similar data set can be identified in the data collection, the test data set will be associated with the said medical condition or effect. Consequently, the information obtained from the data collection can be used, e.g., as a reference for the methods of the present invention described above. More preferably, the data collection comprises characteristic values of all biomarkers comprised by any one of the groups recited above.

In light of the foregoing, the present invention encompasses a data storage medium comprising the aforementioned data collection.

The term "data storage medium" as used herein encompasses data storage media which are based on single physical entities such as a CD, a CD-ROM, a hard disk, optical storage media, or a diskette. Moreover, the term further includes data storage media consisting of physically separated entities which are operatively linked to each other in a manner as to provide the aforementioned data collection, preferably, in a suitable way for a query search.

The present invention also relates to a system comprising:
(a) means for comparing characteristic values of the at least one biomarker of a sample operatively linked to
(b) a data storage medium as described above.

The term "system" as used herein relates to different means which are operatively linked to each other. Said means may be implemented in a single device or may be physically separated devices which are operatively linked to each other. The means for comparing characteristic values of biomarkers, preferably, based on an algorithm for comparison as mentioned before. The data storage medium, preferably, comprises the aforementioned data collection or database, wherein each of the stored data sets being indicative for a medical condition or effect referred to above. Thus, the system of the present invention allows identifying whether a test data set is comprised by the data collection stored in the data storage medium. Consequently, the methods of the present invention can be implemented by the system of the present invention.

In a preferred embodiment of the system, means for determining characteristic values of biomarkers of a sample are comprised. The term "means for determining characteristic values of biomarkers" preferably relates to the aforementioned devices for the determination of metabolites such as mass spectrometry devices, NMR devices or devices for carrying out chemical or biological assays for the biomarkers.

Moreover, the present invention relates to a diagnostic means comprising means for the determination of at least one biomarker selected from any one of the groups referred to above.

The term "diagnostic means", preferably, relates to a diagnostic device, system or biological or chemical assay as specified elsewhere in the description in detail.

The expression "means for the determination of at least one biomarker" refers to devices or agents which are capable of specifically recognizing the biomarker. Suitable devices may be spectrometric devices such as mass spectrometry, NMR devices or devices for carrying out chemical or biological assays for the biomarkers. Suitable agents may be compounds which specifically detect the biomarkers. Detection as used herein may be a two-step process, i.e. the compound may first bind specifically to the biomarker to be detected and subsequently generate a detectable signal, e.g., fluorescent signals, chemiluminescent signals, radioactive signals and the like. For the generation of the detectable signal further compounds may be required which are all comprised by the term "means for determination of the at least one biomarker. Compounds which specifically bind to the biomarker are described elsewhere in the specification in detail and include, preferably, enzymes, antibodies, ligands, receptors or other biological molecules or chemicals which specifically bind to the biomarkers.

Further, the present invention relates to a diagnostic composition comprising at least one biomarker selected from any one of the groups referred to above.

The at least one biomarker selected from any of the aforementioned groups will serve as a biomarker, i.e. an indicator molecule for a medical condition or effect in the subject as set forth elsewhere herein. Thus, the biomarker molecules itself may serve as diagnostic compositions, preferably, upon visualization or detection by the means referred to in herein. Thus, a diagnostic composition which indicates the presence of a biomarker according to the present invention may also comprise the said biomarker physically, e.g., a complex of an antibody and the biomarker to be detected may serve as the diagnostic composition. Accordingly, the diagnostic composition may further comprise means for detection of the metabolites as specified elsewhere in this description. Alternatively, if detection means such as MS or NMR based techniques are used, the molecular species which serves as an indicator for the risk condition will be the at least one biomarker comprised by the test sample to be investigated. Thus, the at least one biomarker referred to in accordance with the present invention shall serve itself as a diagnostic composition due to its identification as a biomarker.

In general, the present invention contemplates the use of at least one biomarker selected from the biomarkers in any one of Tables 1a to c, 3, 4a to c, or 6 in a sample of a subject for diagnosing heart failure, and, preferably, the use of at least one biomarker selected from the biomarkers in any one of Tables 4a to c or 6 in a sample of a subject for diagnosing heart failure according to NYHA class I and the use of at least one biomarker selected from the biomarkers in any one of Tables 1a to c or 3 in a sample of a subject for diagnosing heart failure according to NYHA class I, II and/or III. In case of the biomarkers listed in Tables 3 or 6, the sample shall have been obtained from the subject under exercise. The present invention also contemplates the use of at least one biomarker selected from the any one of Tables 1a or 4a in a sample of a subject for diagnosing dilated cardiomyopathy, the use of at least one biomarker selected from the any one of Tables 1b or 4b in a sample of a subject for diagnosing ischemic cardiomyopathy and/or dilatative cardiomyopathy and the use of at least one biomarker selected from the any one of Tables 1c or 4c in a sample of a subject for diagnosing hypertrophic cardiomyopathy and/or dilatative cardiomyopathy.

Moreover, the present invention pertains to the use, in general, of a ratio of at least one biomarker selected from any one of Tables 2 or 5 calculated from a first and a second sample of a subject for diagnosing heart failure. Preferably, heart failure according to NYHA class I can be diagnosed by the biomarkers of Table 5, while heart failure according to NYHA class I, II and/or III can be diagnosed by the biomarkers of Table 2. It will be understood that the ratio of at least one biomarker shall have been calculated from a first and a second sample obtained from the subject at rest and under exercise.

All references cited herein are herewith incorporated by reference with respect to their disclosure content in general or with respect to the specific disclosure contents indicated above.

The invention will now be illustrated by the following Examples which are not intended to restrict or limit the scope of this invention.

EXAMPLES

The invention will now be illustrated by the following Examples which are not intended to restrict or limit the scope of this invention.

Example 1

Study Design for DCMP (Dilated Cardiomyopathy) and Preparation of Samples 22 male patients suffering from dilated cardiomyopathy and 19 healthy male controls were included in the study.

NYHA (New York Heart Association) scores of the patients ranged from 1-3, and the left ventricular ejection fraction (LVEF) from 10-55%. Patients and controls were matched for age and BMI. For all patients and controls, a blood sample was drawn before (t0) or immediately after (t1) spiroergometer exercise testing. A third blood sample was obtained one hour after exercise testing (t2). Plasma was prepared from all samples by centrifugation, and samples were stored at −80° C. until measurements were performed. Spiroergometry was performed as follows: At the beginning, a load of 15 Watt was applied which was increased every 2 minutes for additional 15 Watt. For all patients, the volume of breath per minute (VE), oxygen uptake ($VO_2$), carbon dioxide emission ($VCO_2$) as well as the frequency of breathing was determined. A respiratory ratio was calculated as follows: $RQ=VCO_2/VO_2$. Breathing equivalents were calculated for $O_2$ ($AÄO_2=VE/VO_2$), for $CO_2$ ($=VE/VCO_2$). The volume per breath (AZV=VE/AF) was calculated as well. Spiroergometry was aborted if the patient was exhausted, if cardiac arrhythmia occurred (e.g., atrial fluttering, blockade of higher order conduct ways, increased ventricular extrasystoles, permanent ventricular tachycardy), if signs of myocardial ischemia could be determined clinically or by electrocardiography, or after application of a load of 285 Watt. Duration of the spiroergometry testing varied between 2 and 38 minutes.

Patients with apparent dilated cardiomyopathy were included if they exhibited a LVEF of <55% and symptoms according to NYHA I to III. NYHA IV patients were excluded as well as patients suffering from apoplex, patients who had myocardial infarction within the last 4 month before testing, patients with altered medications within the last 4 weeks before testing as well as patients who suffered from acute or chronic inflammatory diseases and malignant tumours.

Example 2

Study Design for the Differentiation of CHF Subtypes DCMP (Dilated Cardiomyopathy), ICMP (Ischemic Cardiomyopathy) and HCMP (Hypertrophic Cardiomyopathy) from Healthy Controls The study comprised 81 male and female DCMP-, 81 male and female ICMP- and 80 male and female HCMP patients as well as 83 male and female healthy controls in an age range from 35-75 and a BMI rage from 20-35 kg/m2 were included. NYHA (New York Heart Association) scores of the patients ranged from 1-3. Patients and controls were matched for age, gender and BMI. For all patients and controls, a blood sample was collected. Plasma was prepared by centrifugation, and samples were stored at −80° C. until measurements were performed.

Three subgroups of CHF (DCMP, ICMP and HCMP) were defined on the basis of echocardiography and hemodynamic criteria:
  a) Subgroup DCMP: is hemodynamically defined as a systolic pump failure with cardiomegaly (echocardiographic enhancement of the left ventricular end diastolic diameter >55 mm and a restricted left ventricular ejection fraction—LVEF of <50%).
  b) Subgroup ICMP: is hemodynamically defined as systolic pump failure due to a coronary insufficiency (>50% coronary stenosis and a stress inducible endocardium motion insufficiency as well as an LVEF of <50%)
  c) Subgroup HCMP: concentric heart hypertrophy (echocardiography—septum >11 mm, posterior myocardial wall >11 mm) and with a diastolic CHF (non or mildly impaired pump function with LVEF of ≥50%).

NYHA IV patients were excluded as well as patients suffering from apoplex, patients who had myocardial infarction within the last 4 months before testing, patients with altered medications within the last 4 weeks before testing as well as patients who suffered from acute or chronic inflammatory diseases and malignant tumours.

Example 3

Determination of Metabolites

Human Plasma Samples were Prepared and Subjected to LC-MS/MS and GC-MS or SPE-LC-MS/MS (Hormones) Analysis as Described in the Following:

Proteins were separated by precipitation from blood plasma. After addition of water and a mixture of ethanol and dichlormethan the remaining sample was fractioned into an aqueous, polar phase and an organic, lipophilic phase.

For the transmethanolysis of the lipid extracts a mixture of 140 µl of chloroform, 37 µl of hydrochloric acid (37% by weight HCl in water), 320 µl of methanol and 20 µl of toluene was added to the evaporated extract. The vessel was sealed tightly and heated for 2 hours at 100° C., with shaking. The solution was subsequently evaporated to dryness. The residue was dried completely.

The methoximation of the carbonyl groups was carried out by reaction with methoxyamine hydrochloride (20 mg/ml in pyridine, 100 µl for 1.5 hours at 60° C.) in a tightly sealed vessel. 20 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 100 µl of N-methyl-N-(trimethylsilyl)-2,2,2-trifluoroacetamide (MSTFA) was carried out for 30 minutes at 60° C., again in the tightly sealed vessel. The final volume before injection into the GC was 220 µl.

For the polar phase the derivatization was performed in the following way: The methoximation of the carbonyl groups was carried out by reaction with methoxyamine hydrochloride (20 mg/ml in pyridine, 50 µl for 1.5 hours at 60° C.) in a tightly sealed vessel. 10 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 50 µl of N-methyl-N-(trimethylsilyl)-2,2,2-trifluoroacetamide (MSTFA) was carried out for 30 minutes at 60° C., again in the tightly sealed vessel. The final volume before injection into the GC was 110 µl.

The GC-MS systems consist of an Agilent 6890 GC coupled to an Agilent 5973 MSD. The autosamplers are CompiPal or GCPal from CTC.

For the analysis usual commercial capillary separation columns (30 m×0.25 mm×0.25 µm) with different poly-methylsiloxane stationary phases containing 0% up to 35% of aromatic moieties, depending on the analysed sample materials and fractions from the phase separation step, were used (for example: DB-1 ms, HP-5 ms, DB-XLB, DB-35 ms, Agilent Technologies). Up to 1 µL of the final volume was injected splitless and the oven temperature program was started at 70° C. and ended at 340° C. with different heating rates depending on the sample material and fraction from the phase separation step in order to achieve a sufficient chromatographic separation and number of scans within each analyte peak. Furthermore RTL (Retention Time Locking, Agilent Technologies) was used for the analysis and usual GC-MS standard conditions, for example constant flow with nominal 1 to 1.7 ml/min. and helium as the mobile phase gas, ionisation was done by electron impact with 70 eV, scanning within a m/z range from 15 to 600 with scan rates from 2.5 to 3 scans/sec and standard tune conditions.

The HPLC-MS systems consisted of an Agilent 1100 LC system (Agilent Technologies, Waldbronn, Germany) coupled with an API 4000 Mass spectrometer (Applied Biosystem/MDS SCIEX, Toronto, Canada). HPLC analysis was performed on commercially available reversed phase separation columns with C18 stationary phases (for example: GROM ODS 7 pH, Thermo Betasil C18). Up to 10 µL of the final sample volume of evaporated and reconstituted polar and lipophilic phase was injected and separation was performed with gradient elution using methanol/water/formic acid or acetonitrile/water/formic acid gradients at a flowrate of 200 µL/min.

Mass spectrometry was carried out by electrospray ionisation in positive mode for the non-polar fraction and negative mode for the polar fraction using multiple-reaction-monitoring-(MRM)-mode and fullscan from 100-1000 amu.

Steroids and their metabolites were measured by online SPE-LC-MS (Solid phase extraction-LC-MS). Catecholamines and their metabolites were measured by online SPE-LC-MS as described by Yamada et al. (J. Anal. Toxicol. (26), 2002, 17-22). For both catecholamines and related metabolites and steroids and related metabolites, quantification was achieved by means of stable-isotope-labelled standards, and absolute concentrations were calculated.

Analysis of Complex Lipids in Plasma Samples:

Total lipids were extracted from plasma by liquid/liquid extraction using chloroform/methanol.

The lipid extracts were subsequently fractionated by normal phase liquid chromatography (NPLC) into eleven different lipid groups according to Christie (Journal of Lipid Research (26), 1985, 507-512).

The fractions were analyzed by LC-MS/MS using electrospray ionization (ESI) and atmospheric pressure chemical ionization (APCI) with detection of specific multiple reaction monitoring (MRM) transitions for cholesterol esters (CE) sphingoymelins (SM), and ceramides (CER) respectively. Sphingosines and sphingosine-1-phosphates (SP) were analyzed by LC-MS/MS using electrospray ionization (ESI) with detection of specific multiple reaction monitoring (MRM) transitions as described by Schmidt H et.al., Prostaglandins & other Lipid Mediators 81(2006), 162-170. Metabolites in tables 1a, 1b, 1c, 4a, 4b and 4c, derived from one of these fractions include the respective abbreviation in their name.

Eicosanoids and related were measured out of plasma by offline- and online-SPE LC-MS/MS (Solid phase extraction-LC-MS/MS) (Masoodi M and Nicolaou A: Rapid Commun Mass Spectrom. 2006; 20(20): 3023-3029. Absolute quantification was performed by means of stable isotope-labelled standards.

Example 4

Data Analysis and Statistical Evaluation

Plasma samples were analyzed in randomized analytical sequence design with pooled samples (so called "pool") generated from aliquots of each sample. Following comprehensive analytical validation steps, the raw peak data for each analyte were normalized to the median of pool per analytical sequence to account for process variability (so called "pool-normalized ratios"). If available, absolute concentrations of metabolites were used for statistical analysis. In all other cases, pool-normalized ratios were used. All data were log 10-transformed to achieve normal distribution.

For the study described in Example 1, a mixed-effects model was designed containing the factors age (numerical), BMI (numerical), diagnosis (CHF, control-reference: control), time point (categorical—t0, t1, t2—reference: t0, before exercise) and interaction time point:diagnosis. All factors except for diagnosis were optional, only included if positively contributing to model quality. Proband (each patient or healthy control) was treated as random factor. Statistical significance was read out from p-values of t-statistics. Direction and strength of regulation were obtained by calculation of ratios of median values for the groups to be compared. Regulation type was determined for each metabolite as "up" for increased (ratios>1) within the respective group (CHF) vs. reference (healthy controls) and "down" for decreased (ratios<1) vs. reference.

In order to identify biomarkers of heart failure, the read-out for diagnosis at the pre-exercise time point t0 was considered (table 1). In order to read out diagnosis effects at time points t1 and t2, additional models were calculated with reference for factor time point set to t1 or t2, respectively. To find biomarkers of heart failure in patients undergoing exercise testing, two different read-outs of the mixed-effects model were analyzed. First, metabolite lists were filtered for significance of factor diagnosis at t1 but not at t0 (see table 3). Alternatively, p-values for interaction time point:diagnosis were read out at time point t1 (reference time point t0) (see table 2).

Additional mixed-effect models were calculated to identify metabolites indicative of mild heart failure (NYHA score I). For this purpose, the models mentioned above were modified to contain a fixed factor NYHA score (categorical, reference healthy control) instead of diagnosis (CHF, control-reference: control). As indicator of significance, p-values of t-statistic for NYHA score were read out at level NYHA 1 (tables 4a to c). To find biomarkers of mild heart failure (NYHA score 1) in patients undergoing exercise testing, two different read-outs of the mixed-effects model were analyzed. First, metabolite lists were filtered for significance of factor NYHA score at level NYHA 1, at t1 but not at t0 (see table 6). Second, p-values for interaction time point:NYHA score were read out at level NYHA score 1, time point t1 (reference time point t0) (see table 5).

The study described in Example 2 was analyzed by an ANOVA model comprising factors age, BMI, gender (including all binary interactions), diagnostic group and storage time (optional). Levels for the factor diagnostic group were CHF subtype (DCMP, ICMP, HCMP, control-reference: control). To identify a metabolic profile of early-stage DCMP, analysis was restricted to NYHA I patients (result tables 4a to c). In this case, levels for the factor diagnostic group were DCMP NYHA I, DCMP NYHA II-III, ICMP NYHA I, ICMP NYHA II-III, HCMP NYHA I, HCMP NYHA II-III and control (set as reference).

In tables 1-6, ratio of median indicates strength and direction of regulation. Ratio of median was calculated by dividing the median of metabolite level in the CHF group by the median of metabolite level in the healthy control group. For tables 2 and 5, t0-normalized data (metabolite level at time point t1 divided by metabolite level at time point t0) were used for calculation.

The results of the analyses are summarized in the following tables, below. The biomarkers to be determined in accordance with the methods of the present invention are listed in the following tables. Biomarkers not precisely defined by their name are further characterized in table 7.

TABLE 1a

Metabolites with a significant difference (p-value <0.05) between patients with CHF (dilated cardiomyopathy) and healthy controls

| Metabolite_Name | ratio of median | regulation | p-value |
|---|---|---|---|
| Lysophosphatidylcholine (C18:2) | 0.656 | down | 0.000002 |
| Mannose | 1.949 | up | 0.000000 |
| Hypoxanthine | 2.136 | up | 0.000006 |
| Phytosphingosine | 0.779 | down | 0.000010 |
| Lignoceric acid (C24:0) | 0.654 | down | 0.000029 |
| Glutamate | 2.027 | up | 0.000037 |
| 2-Hydroxybutyrate | 1.724 | up | 0.000132 |
| Lysophosphatidylcholine (C18:0) | 0.820 | down | 0.000213 |
| Behenic acid (C22:0) | 0.744 | down | 0.000224 |
| Tricosanoic acid (C23:0) | 0.708 | down | 0.000237 |
| Phosphatidylcholine (C18:0, C18:2) | 1.028 | up | 0.000248 |
| Linoleic acid (C18:cis[9,12]2) | 0.733 | down | 0.000270 |
| Pseudouridine | 1.299 | up | 0.000321 |
| Phosphate, lipid fraction | 0.817 | down | 0.000333 |
| Lysophosphatidylcholine (C18:1) | 0.874 | down | 0.000432 |
| Lysophosphatidylcholine (C17:0) | 0.770 | down | 0.000612 |
| erythro-Sphingosine (*1) | 0.823 | down | 0.000620 |
| Glycerol phosphate, lipid fraction | 0.768 | down | 0.000628 |
| 5-O-Methylsphingosine (*1) | 0.802 | down | 0.000766 |
| Galactose, lipid fraction | 0.775 | down | 0.000846 |
| Cholesterol | 0.855 | down | 0.000921 |
| alpha-Ketoglutarate | 1.235 | up | 0.000944 |
| Histidine | 0.790 | down | 0.000945 |
| Eicosanoic acid (C20:0) | 0.835 | down | 0.001148 |
| 3-O-Methylsphingosine (*1) | 0.769 | down | 0.001248 |
| erythro-C16-Sphingosine | 0.827 | down | 0.001492 |
| Uric acid | 1.429 | up | 0.001696 |
| Cholesterol No 02 | 0.821 | down | 0.004244 |
| Urea | 1.243 | up | 0.005073 |
| Adrenaline (Epinephrine) | 1.926 | up | 0.006118 |
| Aspartate | 1.120 | up | 0.006265 |
| Normetanephrine | 1.262 | up | 0.006469 |
| Pentadecanol | 0.583 | down | 0.006875 |
| myo-Inositol, lipid fraction | 0.775 | down | 0.007379 |
| Dehydroepiandrosterone sulfate | 0.594 | down | 0.007754 |
| Phosphatidylcholine (C16:1, C18:2) | 0.883 | down | 0.008776 |
| Sphingomyelin (d18:1, C24:0) | 0.943 | down | 0.011533 |
| Threonine | 0.855 | down | 0.012287 |
| myo-Inositol-2-phosphate, lipid fraction (myo-Inositolphospholipids) | 0.635 | down | 0.012637 |
| Myristic acid (C14:0) | 0.572 | down | 0.015030 |
| Homovanillic acid (HVA) | 1.292 | up | 0.015937 |
| Arginine | 0.844 | down | 0.016192 |
| Glutamine | 0.850 | down | 0.016336 |
| Elaidic acid (C18:trans[9]1) | 1.267 | up | 0.017401 |
| 4-Hydroxy-3-methoxyphenylglycol (HMPG) | 1.128 | up | 0.019069 |
| Cystine | 1.105 | up | 0.020208 |
| 4-Hydroxy-3-methoxymandelic acid | 1.179 | up | 0.020480 |
| Zeaxanthin | 0.699 | down | 0.021888 |
| Glucose | 1.215 | up | 0.023219 |
| Stearic acid (C18:0) | 0.918 | down | 0.023703 |
| Cortisol | 1.345 | up | 0.025615 |
| 3-Methoxytyrosine | 1.209 | up | 0.026958 |
| 5-Hydroxy-3-indoleacetic acid (5-HIAA) | 1.255 | up | 0.027467 |
| Lysophosphatidylcholine (C20:4) | 0.944 | down | 0.029167 |
| Creatinine | 1.208 | up | 0.031253 |
| Heptadecanoic acid (C17:0) | 0.828 | down | 0.032349 |
| Proline | 0.818 | down | 0.033617 |
| Erythrol | 1.224 | up | 0.035087 |
| Nervonic acid (C24:cis[15]1) | 0.879 | down | 0.035240 |
| Coenzyme Q10 | 1.060 | up | 0.036613 |
| Coenzyme Q9 | 0.774 | down | 0.040228 |
| Phosphatidylcholine (C18:0, C18:1) | 0.966 | down | 0.044253 |
| Cryptoxanthin | 0.464 | down | 0.047617 |
| 1,5-Anhydrosorbitol | 0.808 | down | 0.047807 |
| SM_Sphingomyelin (d17:1, C24:0) | 0.7142 | down | 2.8E-13 |
| SM_Sphingomyelin (d17:1, C22:0) | 0.7423 | down | 9.8E-12 |
| SM_Sphingomyelin (d17:1, C23:0) | 0.6392 | down | 1.4E-11 |
| CE_Cholesterylester C15:0 | 0.6745 | down | 8.8E-11 |
| Cholesterylester C18:2 | 0.7013 | down | 2.1E-10 |
| SM_Sphingomyelin (d16:1, C23:0) | 0.7103 | down | 2.7E-10 |
| Isocitrate | 1.2983 | up | 4.6E-10 |
| 1-Hydroxy-2-amino-(cis,trans)-3,5-octadecadiene (from sphingolipids) | 0.738 | down | 1.2E-09 |
| Noradrenaline (Norepinephrine) | 1.5067 | up | 4.9E-09 |

TABLE 1a-continued

Metabolites with a significant difference (p-value <0.05) between patients with CHF (dilated cardiomyopathy) and healthy controls

| Metabolite_Name | ratio of median | regulation | p-value |
|---|---|---|---|
| SM_Sphingomyelin (d16:1, C22:0) | 0.7499 | down | 8.7E−09 |
| SM_Sphingomyelin (d16:1, C24:0) | 0.6773 | down | 1.1E−08 |
| Maltose | 1.8136 | up | 1.9E−08 |
| SM_Sphingomyelin (d18:2, C23:0) | 0.8134 | down | 2.7E−08 |
| SM_Sphingomyelin (d17:1, C20:0) | 0.7884 | down | 3E−08 |
| SM_Sphingomyelin (d17:1, C16:0) | 0.8169 | down | 1.6E−07 |
| SM_Sphingomyelin (d18:1, C14:0) | 0.8274 | down | 2.5E−07 |
| CE_Cholesterylester C14:0 | 0.7641 | down | 5.2E−07 |
| Sphingomyelin (d18:1, C23:0) | 0.8793 | down | 6.2E−07 |
| CER_Ceramide (d17:1, C24:0) | 0.7452 | down | 1.7E−06 |
| SM_Sphingomyelin (d18:2, C24:0) | 0.834 | down | 2.3E−06 |
| Uridine | 0.7617 | down | 3.4E−06 |
| CER_Ceramide (d18:2, C14:0) | 0.7732 | down | 6.9E−06 |
| CER_Ceramide (d17:1, C23:0) | 0.7443 | down | 9E−06 |
| SM_Sphingomyelin (d16:1, C20:0) | 0.8091 | down | 1E−05 |
| SM_Sphingomyelin (d17:1, C24:1) | 0.8482 | down | 2.2E−05 |
| SM_Sphingomyelin (d17:1, C18:0) | 0.8393 | down | 3E−05 |
| CE_Cholesterylester C22:6 | 0.7561 | down | 3.3E−05 |
| SM_Sphingomyelin (d16:1, C22:1) | 0.8034 | down | 3.6E−05 |
| myo-Inositol | 1.16 | up | 4.6E−05 |
| CER_Ceramide (d16:1, C24:0) | 0.762 | down | 6.7E−05 |
| beta-Carotene | 0.7066 | down | 8.1E−05 |
| SM_Sphingomyelin (d16:1, C24:1) | 0.8446 | down | 0.00011 |
| Ornithine | 1.1516 | up | 0.00012 |
| SM_Sphingomyelin (d18:2, C22:0) | 0.8501 | down | 0.00013 |
| Cholesta-2,4,6-triene | 0.8494 | down | 0.00016 |
| TAG (C16:0, C18:2) | 1.3317 | up | 0.00017 |
| CE_Cholesterylester C16:2 | 0.7746 | down | 0.00017 |
| CE_Cholesterylester C20:5 | 0.7085 | down | 0.00018 |
| Sorbitol | 1.5523 | up | 0.00019 |
| SM_Sphingomyelin (d18:2, C23:1) | 0.8561 | down | 0.00021 |
| Isopalmitic acid (C16:0) | 0.7684 | down | 0.00022 |
| Sarcosine | 1.1039 | up | 0.00024 |
| Phosphatidylcholine (C18:2, C20:4) | 0.9367 | down | 0.00025 |
| CER_Ceramide (d18:1, C14:0) | 0.8316 | down | 0.00026 |
| SM_Sphingomyelin (d16:1, C18:1) | 0.8335 | down | 0.00031 |
| Sphingosine-1-phosphate (d17:1) | 0.8268 | down | 0.00032 |
| TAG (C16:0, C18:1, C18:2) | 1.4134 | up | 0.00034 |
| SM_Sphingomyelin (d16:1, C21:0) | 0.8077 | down | 0.00038 |
| CER_Ceramide (d16:1, C23:0) | 0.7763 | down | 0.00038 |
| Docosahexaenoic acid (C22:cis[4,7,10,13,16,19]6) | 0.7778 | down | 0.00044 |
| TAG (C18:1, C18:2) | 1.3426 | up | 0.00053 |
| Tyrosine | 1.1292 | up | 0.00057 |
| Testosterone | 0.7956 | down | 0.00059 |
| threo-Sphingosine (*1) | 0.8766 | down | 0.00078 |
| Phenylalanine | 1.0929 | up | 0.00081 |
| CE_Cholesterylester C14:1 | 0.68 | down | 0.00082 |
| Cholesta-2,4-dien | 0.8533 | down | 0.00096 |
| SM_Sphingomyelin (d16:1, C16:0) | 0.8766 | down | 0.00114 |
| Malate | 1.1907 | up | 0.00116 |
| SM_Sphingomyelin (d18:1, C22:0) | 0.8379 | down | 0.00119 |
| CE_Cholesterylester C16:3 | 0.7918 | down | 0.00122 |
| 5-Oxoproline | 1.0814 | up | 0.00123 |
| CE_Cholesterylester C22:5 | 0.8603 | down | 0.00125 |
| SM_Sphingomyelin (d18:1, C23:1) | 0.8878 | down | 0.00132 |
| Docosapentaenoic acid (C22:cis[7,10,13,16,19]5) | 0.8085 | down | 0.00165 |
| CER_Ceramide (d17:1, C16:0) | 0.8577 | down | 0.00176 |
| Taurine | 1.1928 | up | 0.00178 |
| Phosphatidylcholine (C16:0, C20:5) | 0.9159 | down | 0.00195 |
| SM_Sphingomyelin (d18:2, C14:0) | 0.871 | down | 0.00207 |
| Cholesterylester C18:1 | 0.8256 | down | 0.00219 |
| CER_Ceramide (d17:1, C22:0) | 0.8324 | down | 0.00247 |
| CE_Cholesterylester C18:3 | 0.7933 | down | 0.00311 |
| CER_Ceramide (d18:1, C18:0) | 1.1562 | up | 0.00456 |
| SM_Sphingomyelin (d18:2, C21:0) | 0.8893 | down | 0.00466 |
| CE_Cholesterylester C18:4 | 0.7197 | down | 0.00569 |
| SM_Sphingomyelin (d16:1, C18:0) | 0.8762 | down | 0.0057 |
| Glycerol-3-phosphate, polar fraction | 1.159 | up | 0.00613 |
| Cholesterylester C16:0 | 0.8225 | down | 0.00685 |
| Eicosapentaenoic acid (C20:cis[5,8,11,14,17]5) | 0.7853 | down | 0.00809 |
| CE_Cholesterylester C12:0 | 0.7224 | down | 0.00887 |
| trans-4-Hydroxyproline | 1.2178 | up | 0.0089 |
| SM_Sphingomyelin (d18:1, C21:0) | 0.9157 | down | 0.00945 |
| CER_Ceramide (d18:2, C23:0) | 0.869 | down | 0.00948 |
| TAG (C16:0, C16:1) | 1.2811 | up | 0.01131 |

TABLE 1a-continued

Metabolites with a significant difference (p-value <0.05) between patients with CHF (dilated cardiomyopathy) and healthy controls

| Metabolite_Name | ratio of median | regulation | p-value |
|---|---|---|---|
| Glycerol, lipid fraction | 1.2809 | up | 0.01216 |
| CER_Ceramide (d16:1, C16:0) | 0.8776 | down | 0.0122 |
| Cysteine | 1.0714 | up | 0.01409 |
| Phosphatidylcholine (C16:0, C20:4) | 0.991 | down | 0.01571 |
| 8-Hydroxyeicosatetraenoic acid (C20:trans[5]cis[9,11,14]4) (8-HETE) | 1.2207 | up | 0.01617 |
| Hippuric acid | 0.7043 | down | 0.01627 |
| Sphingosine (d18:1) | 1.264 | up | 0.01632 |
| SM_Sphingomyelin (d18:2, C18:1) | 0.9068 | down | 0.01633 |
| Hexadecanol | 1.1092 | up | 0.01765 |
| 14-Methylhexadecanoic acid | 0.8393 | down | 0.01844 |
| CER_Ceramide (d16:1, C22:0) | 0.8608 | down | 0.02052 |
| CER_Ceramide (d18:2, C24:0) | 0.8903 | down | 0.02079 |
| SM_Sphingomyelin (d18:2, C24:2) | 0.9157 | down | 0.02116 |
| Creatine | 1.1628 | up | 0.02211 |
| Eicosenoic acid (C20:cis[11]1) | 1.1674 | up | 0.02337 |
| 14,15-Dihydroxyeicosatrienoic acid (C20:cis[5,8,11]3) | 1.1603 | up | 0.0238 |
| Sphinganine (d18:0) | 1.2016 | up | 0.02412 |
| CER_Ceramide (d18:1, C23:0) | 0.8973 | down | 0.02646 |
| CER_Ceramide (d17:1, C20:0) | 0.876 | down | 0.02705 |
| CER_Ceramide (d18:1, C24:0) | 0.8982 | down | 0.02746 |
| Fumarate | 1.051 | up | 0.03023 |
| SM_Sphingomyelin (d18:2, C20:0) | 0.9289 | down | 0.03273 |
| conjugated Linoleic acid (C18:trans[9,11]2) | 0.8624 | down | 0.03361 |
| 13-Hydroxyoctadecadienoic acid (13-HODE) (C18:cis[9]trans[11]2) | 1.1549 | up | 0.03371 |
| Campesterol | 0.8211 | down | 0.03589 |
| 3,4-Dihydroxyphenylalanine (DOPA) | 1.0983 | up | 0.03675 |
| TAG (C18:2, C18:2) | 1.2038 | up | 0.03696 |
| Phosphatidylcholine No 02 | 0.9467 | down | 0.03922 |
| Glucose-1-phosphate | 1.089 | up | 0.03978 |
| CER_Ceramide (d17:1, C24:1) | 0.8986 | down | 0.04172 |
| Lactaldehyde | 1.0876 | up | 0.04225 |
| Methionine | 1.0698 | up | 0.04311 |
| Lysophosphatidylethanolamine (C22:5) | 0.9229 | down | 0.04472 |
| scyllo-Inositol | 1.1685 | up | 0.04903 |
| CER_Ceramide (d16:1, C21:0) | 0.8656 | down | 0.04997 |

(*1): free and from sphingolipids

TABLE 1b

Metabolites of table 1a which additionally showed a significant difference (p-value <0.1) between ICMP patients and healthy controls

| Metabolite_Name | ratio of median | regulation | p-value |
|---|---|---|---|
| Cholesterylester C18:2 | 0.6066 | down | 3.17E−17 |
| SM_Sphingomyelin (d18:1, C14:0) | 0.7751 | down | 3.88E−11 |
| SM_Sphingomyelin (d18:2, C23:0) | 0.7837 | down | 3.14E−10 |
| SM_Sphingomyelin (d17:1, C23:0) | 0.661 | down | 1.21E−09 |
| Tricosanoic acid (C23:0) | 0.7527 | down | 2.78E−09 |
| CE_Cholesterylester C15:0 | 0.6948 | down | 5.44E−09 |
| SM_Sphingomyelin (d17:1, C24:0) | 0.7656 | down | 1.24E−08 |
| 1-Hydroxy-2-amino-(cis,trans)-3,5-octadecadiene (from sphingolipids) | 0.7463 | down | 1.33E−08 |
| Sorbitol | 1.9715 | up | 3.76E−08 |
| SM_Sphingomyelin (d17:1, C16:0) | 0.8059 | down | 6.53E−08 |
| SM_Sphingomyelin (d16:1, C23:0) | 0.7416 | down | 7.29E−08 |
| beta-Carotene | 0.6178 | down | 1.71E−07 |
| Glutamate | 1.4858 | up | 2.7E−07 |
| CE_Cholesterylester C14:0 | 0.7622 | down | 2.73E−07 |
| SM_Sphingomyelin (d18:2, C23:1) | 0.8017 | down | 4.36E−07 |
| Cholesterylester C18:1 | 0.7308 | down | 4.92E−07 |
| SM_Sphingomyelin (d18:2, C24:0) | 0.82 | down | 6.35E−07 |
| SM_Sphingomyelin (d17:1, C22:0) | 0.8018 | down | 6.9E−07 |
| SM_Sphingomyelin (d18:2, C24:2) | 0.82 | down | 7.56E−07 |
| Lignoceric acid (C24:0) | 0.7793 | down | 8.82E−07 |
| TAG (C16:0, C18:2) | 1.4494 | up | 9.3E−07 |
| threo-Sphingosine (*1) | 0.8271 | down | 1.11E−06 |
| SM_Sphingomyelin (d16:1, C24:0) | 0.7192 | down | 2.4E−06 |

TABLE 1b-continued

Metabolites of table 1a which additionally showed a significant difference
(p-value <0.1) between ICMP patients and healthy controls

| Metabolite_Name | ratio of median | regulation | p-value |
|---|---|---|---|
| Sphingomyelin (d18:1, C23:0) | 0.8821 | down | 2.52E−06 |
| Phosphatidylcholine (C16:0, C20:4) | 0.9828 | down | 2.97E−06 |
| Lysophosphatidylcholine (C17:0) | 0.8091 | down | 3.34E−06 |
| Cholesterol, total | 0.8639 | down | 3.68E−06 |
| SP_Sphingosine-1-phosphate (d17:1) | 0.7871 | down | 4.86E−06 |
| TAG (C16:0, C18:1, C18:2) | 1.5361 | up | 7.11E−06 |
| Glucose | 1.1273 | up | 8.77E−06 |
| SM_Sphingomyelin (d17:1, C24:1) | 0.8464 | down | 1.25E−05 |
| TAG (C18:1, C18:2) | 1.439 | up | 1.53E−05 |
| Isocitrate | 1.2014 | up | 1.7E−05 |
| Phosphatidylcholine (C18:0, C18:2) | 1.0183 | up | 2.19E−05 |
| Zeaxanthin | 0.7372 | down | 2.46E−05 |
| CER_Ceramide (d18:1, C18:0) | 1.2527 | up | 2.54E−05 |
| Cysteine | 1.1313 | up | 2.62E−05 |
| SM_Sphingomyelin (d18:1, C23:1) | 0.8504 | down | 2.65E−05 |
| Behenic acid (C22:0) | 0.839 | down | 2.7E−05 |
| Maltose | 1.5712 | up | 2.99E−05 |
| Uric acid | 1.1916 | up | 2.99E−05 |
| erythro-C16-Sphingosine | 0.7823 | down | 3.62E−05 |
| SM_Sphingomyelin (d18:2, C14:0) | 0.8257 | down | 4.08E−05 |
| Cholesta-2,4-dien | 0.8257 | down | 5.49E−05 |
| Glucose-1-phosphate | 1.1806 | up | 5.61E−05 |
| 5-O-Methylsphingosine (*1) | 0.827 | down | 6.28E−05 |
| Glycerol, lipid fraction | 1.4758 | up | 7E−05 |
| Pseudouridine | 1.1483 | up | 7.79E−05 |
| TAG (C16:0, C16:1) | 1.4548 | up | 0.000109 |
| SM_Sphingomyelin (d18:2, C22:0) | 0.8469 | down | 0.00015 |
| Cholesta-2,4,6-triene | 0.8518 | down | 0.000167 |
| SM_Sphingomyelin (d16:1, C22:0) | 0.8256 | down | 0.00017 |
| SM_Sphingomyelin (d16:1, C24:1) | 0.845 | down | 0.000187 |
| erythro-Sphingosine (*1) | 0.8619 | down | 0.000211 |
| Cystine | 1.2256 | up | 0.00026 |
| Linoleic acid (C18:cis[9,12]2) | 0.8234 | down | 0.000276 |
| 3-O-Methylsphingosine (*1) | 0.839 | down | 0.000315 |
| Taurine | 1.2195 | up | 0.000362 |
| CER_Ceramide (d18:1, C14:0) | 0.8309 | down | 0.000397 |
| Dehydroepiandrosterone sulfate | 0.6197 | down | 0.000427 |
| Lysophosphatidylcholine (C18:2) | 0.8578 | down | 0.000485 |
| 14,15-Dihydroxyeicosatrienoic acid (C20:cis[5,8,11]3) | 1.2659 | up | 0.000573 |
| CER_Ceramide (d17:1, C23:0) | 0.7911 | down | 0.000631 |
| TAG (C18:2, C18:2) | 1.3485 | up | 0.000677 |
| SM_Sphingomyelin (d16:1, C16:0) | 0.8677 | down | 0.000709 |
| Erythrol | 1.1759 | up | 0.000711 |
| CE_Cholesterylester C12:0 | 0.6467 | down | 0.000734 |
| SM_Sphingomyelin (d16:1, C22:1) | 0.8327 | down | 0.000787 |
| Phytosphingosine, total | 0.8621 | down | 0.000895 |
| alpha-Ketoglutarate | 1.1818 | up | 0.000916 |
| 8-Hydroxyeicosatetraenoic acid (C20:trans[5]cis[9,11,14]4) (8-HETE) | 1.3254 | up | 0.001168 |
| CER_Ceramide (d17:1, C24:0) | 0.8152 | down | 0.001205 |
| Cholesterylester C16:0 | 0.788 | down | 0.00143 |
| CE_Cholesterylester C14:1 | 0.7029 | down | 0.001854 |
| SM_Sphingomyelin (d18:1, C22:0) | 0.8429 | down | 0.002434 |
| SM_Sphingomyelin (d18:2, C21:0) | 0.8781 | down | 0.002466 |
| Eicosenoic acid (C20:cis[11]1) | 1.2263 | up | 0.002476 |
| Sarcosine | 1.0878 | up | 0.002491 |
| Adrenaline (Epinephrine) | 1.4435 | up | 0.002549 |
| Galactose, lipid fraction | 0.8964 | down | 0.002702 |
| SM_Sphingomyelin (d17:1, C20:0) | 0.8783 | down | 0.002949 |
| Isoleucine | 1.1085 | up | 0.00385 |
| Isopalmitic acid (C16:0) | 0.8172 | down | 0.003877 |
| CER_Ceramide (d18:2, C14:0) | 0.8446 | down | 0.004044 |
| CE_Cholesterylester C16:2 | 0.8272 | down | 0.004416 |
| Normetanephrine | 1.2896 | up | 0.004728 |
| trans-4-Hydroxyproline | 1.2407 | up | 0.005701 |
| 4-Hydroxy-3-methoxymandelic acid | 1.6034 | up | 0.005745 |
| Mannose | 1.1511 | up | 0.006205 |
| CE_Cholesterylester C22:5 | 0.8782 | down | 0.006918 |
| 5-Oxoproline | 1.0658 | up | 0.007306 |
| myo-Inositol | 1.1023 | up | 0.009187 |
| CE_Cholesterylester C22:6 | 0.8366 | down | 0.009822 |
| SM_Sphingomyelin (d16:1, C21:0) | 0.8596 | down | 0.010056 |
| CER_Ceramide (d16:1, C23:0) | 0.8277 | down | 0.010099 |
| Lysophosphatidylcholine (C18:0) | 0.9017 | down | 0.011903 |

TABLE 1b-continued

Metabolites of table 1a which additionally showed a significant difference (p-value <0.1) between ICMP patients and healthy controls

| Metabolite_Name | ratio of median | regulation | p-value |
|---|---|---|---|
| Ornithine | 1.0943 | up | 0.012027 |
| Noradrenaline (Norepinephrine) | 1.194 | up | 0.01265 |
| SM_Sphingomyelin (d16:1, C18:1) | 0.8798 | down | 0.013795 |
| 3-Methoxytyrosine | 1.1696 | up | 0.016194 |
| Cholestenol No 02 | 0.9013 | down | 0.016563 |
| CE_Cholesterylester C18:3 | 0.8332 | down | 0.01764 |
| CER_Ceramide (d16:1, C24:0) | 0.8487 | down | 0.019382 |
| Sphingomyelin (d18:1, C24:0) | 0.9423 | down | 0.020541 |
| Testosterone | 0.8537 | down | 0.020931 |
| 5-Hydroxy-3-indoleacetic acid (5-HIAA) | 1.1514 | up | 0.021745 |
| CER_Ceramide (d18:2, C23:0) | 0.8822 | down | 0.025435 |
| SM_Sphingomyelin (d18:1, C21:0) | 0.925 | down | 0.026263 |
| Nervonic acid (C24:cis[15]1) | 0.9114 | down | 0.026336 |
| Phenylalanine | 1.0625 | up | 0.0265 |
| Phosphatidylcholine (C16:1, C18:2) | 0.9229 | down | 0.030568 |
| SM_Sphingomyelin (d18:2, C18:1) | 0.9133 | down | 0.0313 |
| CER_Ceramide (d17:1, C16:0) | 0.8986 | down | 0.035021 |
| Cryptoxanthin | 0.8091 | down | 0.036128 |
| Fumarate | 1.0483 | up | 0.036755 |
| Tyrosine | 1.0777 | up | 0.038994 |
| CE_Cholesterylester C20:5 | 0.8236 | down | 0.039914 |
| CE_Cholesterylester C18:4 | 0.7902 | down | 0.043667 |
| Malate | 1.1101 | up | 0.046935 |
| SM_Sphingomyelin (d16:1, C20:0) | 0.9095 | down | 0.053287 |
| CER_Ceramide (d17:1, C22:0) | 0.8882 | down | 0.057993 |
| Glycerol-3-phosphate, polar fraction | 1.1093 | up | 0.061765 |
| Uridine | 0.8946 | down | 0.062565 |
| SM_Sphingomyelin (d17:1, C18:0) | 0.9258 | down | 0.072709 |
| Hippuric acid | 0.7791 | down | 0.081397 |
| CER_Ceramide (d18:1, C23:0) | 0.9177 | down | 0.089112 |
| Phosphate, lipid fraction | 0.9505 | down | 0.097734 |

(*1): free and from sphingolipids

TABLE 1c

Metabolites of Table 1a which additionally showed a significant difference (p-value <0.1) between HCMP patients and healthy controls

| Metabolite_Name | ratio of median | regulation | p-value |
|---|---|---|---|
| Maltose | 2.1427 | up | 5.39E−11 |
| Cholesterylester C18:2 | 0.7523 | down | 1.99E−06 |
| Cholesterylester C18:1 | 0.7715 | down | 5.23E−05 |
| Taurine | 1.2525 | up | 9.72E−05 |
| TAG (C16:0, C18:2) | 1.2934 | up | 0.00091 |
| Uric acid | 1.1564 | up | 0.000939 |
| TAG (C18:1, C18:2) | 1.3302 | up | 0.00099 |
| Glycerol, lipid fraction | 1.3816 | up | 0.001367 |
| TAG (C16:0, C18:1, C18:2) | 1.3509 | up | 0.002192 |
| CE_Cholesterylester C15:0 | 0.8215 | down | 0.002242 |
| SP_Sphingosine-1-phosphate (d17:1) | 0.8497 | down | 0.002442 |
| SP_Sphinganine (d18:0) | 1.2867 | up | 0.002474 |
| SP_Sphingosine (d18:1) | 1.3486 | up | 0.002704 |
| Sarcosine | 1.0901 | up | 0.003105 |
| beta-Carotene | 0.7568 | down | 0.003481 |
| Cysteine | 1.0924 | up | 0.003905 |
| Tricosanoic acid (C23:0) | 0.8682 | down | 0.004041 |
| TAG (C16:0, C16:1) | 1.3303 | up | 0.004263 |
| Eicosenoic acid (C20:cis[11]1) | 1.2145 | up | 0.005339 |
| Isoleucine | 1.1098 | up | 0.005399 |
| Sphingomyelin (d18:1, C23:0) | 0.926 | down | 0.005483 |
| SM_Sphingomyelin (d18:2, C23:0) | 0.897 | down | 0.006161 |
| Noradrenaline (Norepinephrine) | 1.2232 | up | 0.006926 |
| Lysophosphatidylcholine (C17:0) | 0.8834 | down | 0.008806 |
| Testosterone | 0.8292 | down | 0.009379 |
| TAG (C18:2, C18:2) | 1.2656 | up | 0.009482 |

TABLE 1c-continued

Metabolites of Table 1a which additionally showed a significant difference (p-value <0.1) between HCMP patients and healthy controls

| Metabolite_Name | ratio of median | regulation | p-value |
|---|---|---|---|
| Isocitrate | 1.1189 | up | 0.011414 |
| SM_Sphingomyelin (d17:1, C24:0) | 0.885 | down | 0.011423 |
| SM_Sphingomyelin (d17:1, C23:0) | 0.8387 | down | 0.011783 |
| Zeaxanthin | 0.8283 | down | 0.012366 |
| SM_Sphingomyelin (d16:1, C23:0) | 0.869 | down | 0.014315 |
| Cryptoxanthin | 0.7778 | down | 0.018169 |
| Erythrol | 1.121 | up | 0.023299 |
| CER_Ceramide (d17:1, C23:0) | 0.8563 | down | 0.030171 |
| Cholesterylester C16:0 | 0.8446 | down | 0.030834 |
| SM_Sphingomyelin (d17:1, C22:0) | 0.9062 | down | 0.032352 |
| SM_Sphingomyelin (d18:1, C21:0) | 0.9242 | down | 0.032429 |
| SM_Sphingomyelin (d16:1, C21:0) | 0.8795 | down | 0.034803 |
| Glucose | 1.0597 | up | 0.035437 |
| Glutamate | 1.1813 | up | 0.036213 |
| Fumarate | 1.0499 | up | 0.03758 |
| SM_Sphingomyelin (d17:1, C20:0) | 0.9101 | down | 0.039401 |
| CE_Cholesterylester C14:0 | 0.8974 | down | 0.044159 |
| Cystine | 1.1237 | up | 0.044881 |
| 8-Hydroxyeicosatetraenoic acid (C20:trans[5]cis[9,11,14]4) (8-HETE) | 1.1957 | up | 0.047092 |
| 1-Hydroxy-2-amino-(cis,trans)-3,5-octadecadiene (from sphingolipids) | 0.9003 | down | 0.047207 |
| Uridine | 0.8827 | down | 0.047309 |
| Sorbitol | 1.2852 | up | 0.048213 |
| SM_Sphingomyelin (d18:1, C14:0) | 0.9258 | down | 0.049457 |
| Elaidic acid (C18:trans[9]1) | 1.6069 | up | 0.05134 |
| SM_Sphingomyelin (d18:2, C21:0) | 0.9165 | down | 0.052457 |
| Aspartate | 1.0842 | up | 0.056222 |
| Coenzyme Q10 | 1.1425 | up | 0.068217 |
| CER_Ceramide (d18:1, C18:0) | 1.1056 | up | 0.070545 |
| SM_Sphingomyelin (d17:1, C16:0) | 0.9289 | down | 0.07279 |
| SM_Sphingomyelin (d18:2, C23:1) | 0.9224 | down | 0.073683 |
| Lactaldehyde | 1.0822 | up | 0.078804 |
| Pseudouridine | 1.0653 | up | 0.082343 |
| Hippuric acid | 0.7733 | down | 0.083253 |
| SM_Sphingomyelin (d18:1, C23:1) | 0.9341 | down | 0.088944 |
| CER_Ceramide (d17:1, C24:0) | 0.8949 | down | 0.091594 |
| Glucose-1-phosphate | 1.0739 | up | 0.091687 |
| SM_Sphingomyelin (d18:2, C24:0) | 0.933 | down | 0.092261 |

TABLE 2

Metabolites with a significant difference (p-value <0.05) in exercise-induced change between CHF and control

| Metabolite | ratio of median | regulation | p-value |
|---|---|---|---|
| Glutamate | 0.724 | down | 0.000274 |
| Hypoxanthine | 0.448 | down | 0.000276 |
| Adrenaline (Epinephrine) | 0.439 | down | 0.001258 |
| Lactate | 0.612 | down | 0.005556 |
| Indole-3-lactic acid | 1.198 | up | 0.007027 |
| Threonic acid | 1.160 | up | 0.018026 |
| Cholestenol No 02 | 0.906 | down | 0.022576 |
| alpha-Tocotrienol | 1.206 | up | 0.028952 |
| Coenzyme Q9 | 1.166 | up | 0.029375 |
| Histidine | 1.083 | up | 0.039156 |
| Phosphatidylcholine (C18:0, C20:4) | 1.008 | up | 0.039198 |
| Lysophosphatidylcholine (C18:1) | 1.027 | up | 0.040233 |

TABLE 3

Metabolites with a significant difference (p-value <0.05) between patients with CHF and healthy controls at the peak of exercise (t1) but not at rest (t0)

| | Time point | | | | | |
|---|---|---|---|---|---|---|
| Metabolite | t0 ratio of median | t0 regulation | t0 p-value | t1 ratio of median | t1 regulation | t1 p-value |
| Lactate | 1.149 | up | 0.161549 | 0.705 | down | 0.015456 |
| Citrate | 1.118 | up | 0.256634 | 1.132 | up | 0.040482 |

TABLE 4a

Metabolites with a significant difference (p-value <0.05) between patients with CHF (dilated cardiomyopathy) with NYHA score 1 and healthy controls

| Metabolite | ratio of median | regulation | p-value |
|---|---|---|---|
| Mannose | 2.168 | up | 0.000025 |
| Lysophosphatidylcholine (C18:2) | 0.699 | down | 0.000748 |
| Adrenaline (Epinephrine) | 2.411 | up | 0.004448 |
| Hypoxanthine | 1.779 | up | 0.004996 |
| Phosphatidylcholine (C18:0, C18:2) | 1.022 | up | 0.012486 |

TABLE 4a-continued

Metabolites with a significant difference (p-value <0.05) between patients with CHF (dilated cardiomyopathy) with NYHA score 1 and healthy controls

| Metabolite | ratio of median | regulation | p-value |
|---|---|---|---|
| Glucose | 1.271 | up | 0.014916 |
| Phosphate (inorganic and from organic phosphates) | 0.793 | down | 0.015030 |
| Cortisol | 1.340 | up | 0.017261 |
| Phosphatidylcholine (C18:0, C22:6) | 1.239 | up | 0.017614 |
| 2-Hydroxybutyrate | 1.810 | up | 0.019583 |
| Corticosterone | 1.293 | up | 0.019642 |
| Androstenedione | 1.785 | up | 0.035365 |
| Glutamate | 1.333 | up | 0.039299 |
| Pentadecanol | 0.581 | down | 0.044212 |
| Maltose | 1.7858 | up | 8.3846E−06 |
| CE__Cholesterylester C15:0 | 0.7215 | down | 1.073E−05 |
| Cholesterylester C18:2 | 0.7456 | down | 1.7406E−05 |
| SM__Sphingomyelin (d17:1, C24:0) | 0.7957 | down | 2.6209E−05 |
| Noradrenaline (Norepinephrine) | 1.4153 | up | 5.5355E−05 |
| myo-Inositol | 1.1987 | up | 6.44E−05 |
| SM__Sphingomyelin (d17:1, C23:0) | 0.731 | down | 8.1995E−05 |
| SM__Sphingomyelin (d17:1, C22:0) | 0.8196 | down | 0.00013927 |
| Sorbitol | 1.7458 | up | 0.00014037 |
| Normetanephrine | 1.5039 | up | 0.0001699 |
| Isocitrate | 1.2084 | up | 0.00019135 |
| SM__Sphingomyelin (d18:1, C23:0) | 0.8716 | down | 0.00026783 |
| Ornithine | 1.1704 | up | 0.00037428 |
| Erythrol | 1.2249 | up | 0.00040476 |
| Sarcosine | 1.1251 | up | 0.00042563 |
| Cystine | 1.2636 | up | 0.00044298 |
| Testosterone | 0.7586 | down | 0.00086625 |
| CE__Cholesterylester C14:0 | 0.8093 | down | 0.0008742 |
| Uridine | 0.7862 | down | 0.00092815 |
| SM__Sphingomyelin (d18:1, C14:0) | 0.8622 | down | 0.00104019 |
| Lignoceric acid (C24:0) | 0.8223 | down | 0.00134372 |
| Tricosanoic acid (C23:0) | 0.8376 | down | 0.00139431 |
| 1-Hydroxy-2-amino-(cis,trans)-3,5-octadecadiene (from sphingolipids) | 0.8262 | down | 0.00145507 |
| SM__Sphingomyelin (d16:1, C24:0) | 0.7694 | down | 0.00146283 |
| Urea | 1.2149 | up | 0.0015119 |
| beta-Carotene | 0.7083 | down | 0.00164813 |
| Tyrosine | 1.1473 | up | 0.001792 |
| Behenic acid (C22:0) | 0.8547 | down | 0.00192144 |
| alpha-Ketoglutarate | 1.218 | up | 0.00195906 |
| SM__Sphingomyelin (d16:1, C23:0) | 0.8262 | down | 0.00281307 |
| Taurine | 1.2111 | up | 0.00288466 |
| SM__Sphingomyelin (d18:1, C24:0) | 0.8827 | down | 0.0032925 |
| 3-Methoxytyrosine | 1.259 | up | 0.00371589 |
| Lysophosphatidylcholine (C17:0) | 0.8552 | down | 0.00392246 |
| SM__Sphingomyelin (d18:2, C23:0) | 0.8797 | down | 0.00428746 |
| CER__Ceramide (d18:2, C14:0) | 0.8188 | down | 0.00445012 |
| SM__Sphingomyelin (d17:1, C16:0) | 0.8763 | down | 0.00489531 |
| Cholesta-2,4,6-triene | 0.8657 | down | 0.00545382 |
| SM__Sphingomyelin (d18:2, C24:0) | 0.8781 | down | 0.00576839 |
| Phenylalanine | 1.0947 | up | 0.00620035 |
| Cysteine | 1.1 | up | 0.00624402 |
| SM__Sphingomyelin (d16:1, C22:0) | 0.8502 | down | 0.00665211 |
| Uric acid | 1.1441 | up | 0.00696304 |
| CER__Ceramide (d17:1, C24:0) | 0.8237 | down | 0.00931215 |
| Glucose-1-phosphate | 1.1388 | up | 0.00940813 |
| CE__Cholesterylester C22:5 | 0.8609 | down | 0.0095955 |
| CE__Cholesterylester C16:2 | 0.8095 | down | 0.00966362 |
| Dehydroepiandrosterone sulfate | 0.6524 | down | 0.00995067 |
| Glycerol-3-phosphate, polar fraction | 1.1886 | up | 0.00997343 |
| Isoleucine | 1.1158 | up | 0.0102759 |
| SM__Sphingomyelin (d17:1, C20:0) | 0.8765 | down | 0.01056663 |
| CER__Ceramide (d18:1, C14:0) | 0.852 | down | 0.01059946 |
| Cholesterol, total | 0.9069 | down | 0.01060847 |
| SM__Sphingomyelin (d18:1, C22:0) | 0.8438 | down | 0.01179659 |
| Linoleic acid (C18:cis[9,12]2) | 0.8487 | down | 0.01208761 |
| threo-Sphingosine (*1) | 0.8906 | down | 0.01352672 |
| SM__Sphingomyelin (d17:1, C24:1) | 0.9005 | down | 0.01479843 |
| CE__Cholesterylester C16:3 | 0.8114 | down | 0.01621643 |
| CE__Cholesterylester C14:1 | 0.7197 | down | 0.01779781 |
| Cholesterylester C18:1 | 0.837 | down | 0.01841802 |
| scyllo-Inositol | 1.2605 | up | 0.02009089 |
| CE__Cholesterylester C22:6 | 0.8245 | down | 0.02009893 |
| Pseudouridine | 1.0972 | up | 0.02576962 |
| CER__Ceramide (d17:1, C23:0) | 0.8359 | down | 0.02705684 |
| erythro-C16-Sphingosine | 0.8592 | down | 0.02915249 |
| Eicosenoic acid (C20:cis[11]1) | 1.1968 | up | 0.02965701 |
| SP__Sphinganine (d18:0) | 1.2368 | up | 0.03058449 |
| Isopalmitic acid (C16:0) | 0.8326 | down | 0.03139525 |
| Cholesta-2,4-dien | 0.8837 | down | 0.03222468 |
| Lysophosphatidylcholine (C18:0) | 0.8999 | down | 0.03342501 |
| Phosphatidylcholine (C16:1, C18:2) | 0.9093 | down | 0.03389605 |
| Cholesterylester C16:0 | 0.8258 | down | 0.03509819 |
| TAG (C16:0, C18:2) | 1.2113 | up | 0.03532712 |
| SM__Sphingomyelin (d18:2, C22:0) | 0.8964 | down | 0.03540009 |
| CER__Ceramide (d17:1, C16:0) | 0.8814 | down | 0.03839909 |
| Glycerol, lipid fraction | 1.2796 | up | 0.03879761 |
| CE__Cholesterylester C18:3 | 0.8253 | down | 0.04166858 |
| 5-Oxoproline | 1.0601 | up | 0.04385594 |
| CE__Cholesterylester C22:4 | 0.8749 | down | 0.04444786 |
| Serine, lipid fraction | 1.2253 | up | 0.046845 |
| 5-O-Methylsphingosine (*1) | 0.8943 | down | 0.04788647 |
| TAG (C16:0, C18:1, C18:2) | 1.2557 | up | 0.04838256 |
| SP__Sphingosine (d18:1) | 1.2602 | up | 0.04924965 |

(*1): free and from sphingolipids

TABLE 4b

Metabolites of Table 4a which additionally showed a significant difference (p-value <0.1) between ICMP patients with NYHA score 1 and healthy controls

| Metabolite__Name | ratio of median | regulation | p-value |
|---|---|---|---|
| Cholesterylester C18:2 | 0.6118 | down | 1.7191E−12 |
| SM__Sphingomyelin (d18:1, C14:0) | 0.7778 | down | 3.7018E−08 |
| Sorbitol | 2.0982 | up | 4.3743E−07 |
| SM__Sphingomyelin (d18:2, C23:0) | 0.8125 | down | 4.0589E−06 |
| SM__Sphingomyelin (d17:1, C23:0) | 0.7067 | down | 1.1938E−05 |
| CE__Cholesterylester C15:0 | 0.7269 | down | 1.472E−05 |
| SM__Sphingomyelin (d18:1, C23:0) | 0.8512 | down | 1.8295E−05 |
| TAG (C16:0, C18:2) | 1.453 | up | 1.8737E−05 |
| Cholesterylester C18:1 | 0.7343 | down | 1.939E−05 |
| Tricosanoic acid (C23:0) | 0.7919 | down | 2.5541E−05 |
| 1-Hydroxy-2-amino-(cis,trans)-3,5-octadecadiene (from sphingolipids) | 0.7813 | down | 3.8025E−05 |
| Cholesterol, total | 0.8603 | down | 3.8932E−05 |
| TAG (C16:0, C18:1, C18:2) | 1.572 | up | 4.2286E−05 |
| SM__Sphingomyelin (d17:1, C16:0) | 0.8268 | down | 5.0421E−05 |
| CE__Cholesterylester C14:0 | 0.785 | down | 6.3189E−05 |
| beta-Carotene | 0.6577 | down | 0.00012609 |
| threo-Sphingosine (*1) | 0.8433 | down | 0.00014084 |
| Cholesta-2,4-dien | 0.8112 | down | 0.00014837 |
| Lysophosphatidylcholine (C17:0) | 0.8168 | down | 0.00018589 |
| Glucose | 1.1224 | up | 0.00021581 |
| Glutamate | 1.3974 | up | 0.00024219 |
| SM__Sphingomyelin (d17:1, C24:0) | 0.8216 | down | 0.00026196 |
| Lignoceric acid (C24:0) | 0.8114 | down | 0.00031083 |
| SM__Sphingomyelin (d16:1, C23:0) | 0.7977 | down | 0.00038589 |
| Phosphatidylcholine (C18:0, C18:2) | 1.0177 | up | 0.00040589 |
| SM__Sphingomyelin (d18:2, C24:0) | 0.8492 | down | 0.00049962 |
| 5-O-Methylsphingosine (*1) | 0.8249 | down | 0.0006501 |
| SM__Sphingomyelin (d17:1, C22:0) | 0.8428 | down | 0.00094804 |
| Cystine | 1.2438 | up | 0.00096287 |
| Taurine | 1.2299 | up | 0.00120903 |
| Glucose-1-phosphate | 1.1646 | up | 0.00135235 |
| SM__Sphingomyelin (d17:1, C24:1) | 0.8718 | down | 0.00137508 |
| Glycerol, lipid fraction | 1.4351 | up | 0.00147588 |
| Behenic acid (C22:0) | 0.8594 | down | 0.00159109 |
| SM__Sphingomyelin (d16:1, C24:0) | 0.7739 | down | 0.00173184 |
| Isocitrate | 1.1685 | up | 0.00194376 |
| Cysteine | 1.1133 | up | 0.0019666 |

TABLE 4b-continued

Metabolites of Table 4a which additionally showed a significant difference (p-value <0.1) between ICMP patients with NYHA score 1 and healthy controls

| Metabolite_Name | ratio of median | regulation | p-value |
|---|---|---|---|
| 3-Methoxytyrosine | 1.2542 | up | 0.00284987 |
| CER_Ceramide (d18:1, C14:0) | 0.8291 | down | 0.00290481 |
| erythro-C16-Sphingosine | 0.8147 | down | 0.00311066 |
| Linoleic acid (C18:cis[9,12]2) | 0.8385 | down | 0.00451392 |
| Maltose | 1.4331 | up | 0.00496723 |
| Adrenaline (Epinephrine) | 1.5012 | up | 0.00542671 |
| SM_Sphingomyelin (d18:2, C22:0) | 0.8703 | down | 0.00727388 |
| Lysophosphatidylcholine (C18:2) | 0.8695 | down | 0.00744797 |
| Normetanephrine | 1.3345 | up | 0.00759363 |
| SM_Sphingomyelin (d18:1, C24:0) | 0.8937 | down | 0.0076034 |
| Cholesterylester C16:0 | 0.7884 | down | 0.00805685 |
| Eicosenoic acid (C20:cis[11]1) | 1.2302 | up | 0.00826261 |
| Cholesta-2,4,6-triene | 0.8784 | down | 0.00837711 |
| CE_Cholesterylester C22:5 | 0.8605 | down | 0.00891577 |
| Dehydroepiandrosterone sulfate | 0.6661 | down | 0.00966052 |
| Pseudouridine | 1.1119 | up | 0.01037548 |
| CE_Cholesterylester C22:4 | 0.8457 | down | 0.01129319 |
| CE_Cholesterylester C14:1 | 0.7165 | down | 0.01133041 |
| Lysophosphatidylcholine (C18:0) | 0.8831 | down | 0.01177707 |
| Uric acid | 1.1327 | up | 0.01187686 |
| SM_Sphingomyelin (d18:1, C22:0) | 0.8458 | down | 0.01247557 |
| Testosterone | 0.8204 | down | 0.01585512 |
| CER_Ceramide (d17:1, C23:0) | 0.8278 | down | 0.02004195 |
| SM_Sphingomyelin (d16:1, C22:0) | 0.875 | down | 0.0242648 |
| Noradrenaline (Norepinephrine) | 1.2117 | up | 0.02471946 |
| CE_Cholesterylester C16:2 | 0.8476 | down | 0.03239574 |
| 5-Oxoproline | 1.0599 | up | 0.03394216 |
| alpha-Ketoglutarate | 1.1326 | up | 0.03826297 |
| CER_Ceramide (d17:1, C24:0) | 0.8583 | down | 0.04035007 |
| Isopalmitic acid (C16:0) | 0.8489 | down | 0.04227044 |
| CE_Cholesterylester C18:3 | 0.8356 | down | 0.04430951 |
| CE_Cholesterylester C22:6 | 0.8484 | down | 0.04599329 |
| SM_Sphingomyelin (d17:1, C20:0) | 0.9092 | down | 0.06237979 |
| Isoleucine | 1.0817 | up | 0.06356105 |
| Tyrosine | 1.083 | up | 0.06681343 |
| Ornithine | 1.0775 | up | 0.07275574 |
| Phosphatidylcholine (C16:1, C18:2) | 0.9234 | down | 0.0730987 |
| Mannose | 1.1099 | up | 0.07913279 |
| myo-Inositol | 1.08 | up | 0.08438868 |

(*1): free and from sphingolipids

TABLE 4c

Metabolites of Table 4a which additionally showed a significant difference (p-value <0.1) between HCMP patients with NYHA 1 scores and healthy controls

| Metabolite_Name | ratio of median | regulation | p-value |
|---|---|---|---|
| Maltose | 2.3774 | up | 9.1877E-11 |
| Cholesterylester C18:2 | 0.7422 | down | 1.5121E-05 |

TABLE 4c-continued

Metabolites of Table 4a which additionally showed a significant difference (p-value <0.1) between HCMP patients with NYHA 1 scores and healthy controls

| Metabolite_Name | ratio of median | regulation | p-value |
|---|---|---|---|
| Taurine | 1.3057 | up | 4.2799E-05 |
| Cholesterylester C18:1 | 0.7566 | down | 0.00017957 |
| Isoleucine | 1.1583 | up | 0.00067494 |
| TAG (C16:0, C18:2) | 1.3413 | up | 0.00106071 |
| Sarcosine | 1.1148 | up | 0.00123586 |
| SP_Sphinganine (d18:0) | 1.3661 | up | 0.00126025 |
| SP_Sphingosine (d18:1) | 1.4493 | up | 0.00135359 |
| TAG (C16:0, C18:1, C18:2) | 1.4301 | up | 0.00163138 |
| CE_Cholesterylester C15:0 | 0.814 | down | 0.00544571 |
| SM_Sphingomyelin (d18:1, C23:0) | 0.9016 | down | 0.00613976 |
| Tricosanoic acid (C23:0) | 0.8591 | down | 0.00645307 |
| SM_Sphingomyelin (d18:2, C23:0) | 0.8856 | down | 0.00715908 |
| Glycerol, lipid fraction | 1.3643 | up | 0.00800466 |
| Eicosenoic acid (C20:cis[11]1) | 1.2284 | up | 0.01113831 |
| SM_Sphingomyelin (d17:1, C23:0) | 0.8234 | down | 0.01457624 |
| Uric acid | 1.1278 | up | 0.01663987 |
| beta-Carotene | 0.7703 | down | 0.01772396 |
| Serine, lipid fraction | 1.2593 | up | 0.02396587 |
| Testosterone | 0.8387 | down | 0.03444244 |
| CE_Cholesterylester C22:5 | 0.8857 | down | 0.03705511 |
| Noradrenaline (Norepinephrine) | 1.1939 | up | 0.03929456 |
| CE_Cholesterylester C22:4 | 0.8728 | down | 0.04240014 |
| 1-Hydroxy-2-amino-(cis,trans)-3,5-octadecadiene (from sphingolipids) | 0.8851 | down | 0.04256896 |
| Uridine | 0.8639 | down | 0.04452619 |
| Glutamate | 1.199 | up | 0.04801547 |
| Lysophosphatidylcholine (C17:0) | 0.8984 | down | 0.04926739 |
| SM_Sphingomyelin (d16:1, C23:0) | 0.8842 | down | 0.05494844 |
| Cholesterylester C16:0 | 0.8449 | down | 0.06302395 |
| SM_Sphingomyelin (d18:1, C14:0) | 0.9196 | down | 0.06434119 |
| SM_Sphingomyelin (d17:1, C22:0) | 0.9084 | down | 0.0655624 |
| SM_Sphingomyelin (d18:2, C24:0) | 0.9168 | down | 0.06627783 |
| Erythrol | 1.112 | up | 0.06717477 |
| Isocitrate | 1.097 | up | 0.06783798 |
| SM_Sphingomyelin (d17:1, C20:0) | 0.9104 | down | 0.06992485 |
| SM_Sphingomyelin (d17:1, C24:0) | 0.9103 | down | 0.08265925 |
| CER_Ceramide (d18:2, C14:0) | 0.8865 | down | 0.08795584 |

TABLE 5

Metabolites with a significant difference (p-value <0.05) in exercise-induced change between CHF with NYHA score 1 and control

| Metabolite | ratio of median | regulation | p-value |
|---|---|---|---|
| Glutamate | 0.720 | down | 0.025093 |
| Hypoxanthine | 0.407 | down | 0.034843 |
| Phosphatidylcholine (C18:0, C20:4) | 1.011 | up | 0.048864 |

TABLE 6

Metabolites with a significant difference (p-value <0.05) between patients with CHF with NYHA score I at the peak of exercise (t1) but not at rest (t0)

| | Time point | | | | | |
|---|---|---|---|---|---|---|
| | t0 | | | t1 | | |
| Parameter | t0 ratio of median | t0 regulation | t0 p-value | t1 ratio of median | t1 regulation | t1 p-value |
| Phosphatidylcholine (C18:0, C20:4) | 1.035900639 | up | 0.339994 | 1.054274585 | up | 0.049492 |

TABLE 7

Chemical/physical properties of selected analytes. These biomarkers are characterized herein by chemical and physical properties.

| Metabolite | Fragmentation pattern (GC-MS) and description |
| --- | --- |
| Glycerol phosphate, lipid fraction | Glycerol phosphate, lipid fraction represents the sum parameter of metabolites containing a glycerol-2-phosphate or a glycerol-3-phosphate moiety and being present in the lipid fraction after extraction and separation of the extract into a polar and a lipid fraction. |
| 3-O-Methylsphingosine | 3-O-Methylsphingosine exhibits the following characteristic ionic fragments if detected with GC/MS, applying electron impact (EI) ionization mass spectrometry, after acidic methanolysis and derivatisation with 2% O-methylhydroxylamine-hydrochlorid in pyridine and subsequently with N-methyl-N-trimethylsilyltrifluoracetamid: MS (EI, 70 eV): m/z (%): 204 (100), 73 (18), 205 (16), 206 (7), 354 (4), 442 (1). |
| 5-O-Methylsphingosine | 5-O-Methylsphingosine exhibits the following characteristic ionic fragments if detected with GC/MS, applying electron impact (EI) ionization mass spectrometry, after acidic methanolysis and derivatisation with 2% O-methylhydroxylamine-hydrochlorid in pyridine and subsequently with N-methyl-N-trimethylsilyltrifluoracetamid: MS (EI, 70 eV): m/z (%): 250 (100), 73 (34), 251 (19), 354 (14), 355 (4), 442 (1). |
| Phosphatidyl-choline No 02 | Phosphatidylcholine No 02 represents the sum parameter of phosphatidylcholines. It exhibits the following characteristic ionic species when detected with LC/MS, applying electro-spray ionization (ESI) mass spectrometry: mass-to-charge ratio (m/z) of the positively charged ionic species is 808.4 (+/− 0.5). |
| TAG (C16:0, C16:1) | TAG (C16:0, C16:1) represents the sum parameter of triacylglycerides containing the combination of a C16:0 fatty acid unit and a C16:1 fatty acid unit. It exhibits the following characteristic ionic species when detected with LC/MS, applying electro-spray ionization (ESI) mass spectrometry: mass-to-charge ratio (m/z) of the positively charged ionic species is 549.6 (+/− 0.5). |
| TAG (C16:0, C18:2) | TAG (C16:0, C18:2) represents the sum parameter of triacylglycerides containing the combination of a C16:0 fatty acid unit and a C18:2 fatty acid unit. It exhibits the following characteristic ionic species when detected with LC/MS, applying electro-spray ionization (ESI) mass spectrometry: mass-to-charge ratio (m/z) of the positively charged ionic species is 575.6 (+/− 0.5). |
| TAG (C18:1, C18:2) | TAG (C18:1, C18:2) represents the sum parameter of triacylglycerides containing the combination of a C18:1 fatty acid unit and a C18:2 fatty acid unit. It exhibits the following characteristic ionic species when detected with LC/MS, applying electro-spray ionization (ESI) mass spectrometry: mass-to-charge ratio (m/z) of the positively charged ionic species is 601.6 (+/− 0.5). |
| TAG (C18:2, C18:2) | TAG (C18:2, C18:2) represents the sum parameter of triacylglycerides containing the combination of two C18:2 fatty acid units. It exhibits the following characteristic ionic species when detected with LC/MS, applying electro-spray ionization (ESI) mass spectrometry: mass-to-charge ratio (m/z) of the positively charged ionic species is 599.6 (+/− 0.5). |
| Cholestenol No 02 | Cholestenol No 02 represents a Cholestenol isomer. It exhibits the following characteristic ionic fragments if detected with GC/MS, applying electron impact (EI) ionization mass spectrometry, after acidic methanolysis and derivatisation with 2% O-methylhydroxylamine-hydrochlorid in pyridine and subsequently with N-methyl-N-trimethylsilyltrifluoracetamid: MS (EI, 70 eV): m/z (%): 143 (100), 458 (91), 73 (68), 81 (62), 95 (36), 185 (23), 327 (23), 368 (20), 255 (15), 429 (15). |

The invention claimed is:

1. A method for diagnosing heart failure in a subject comprising:

a) detecting in a sample of a subject suspected to suffer from heart failure, but not exhibiting heart failure symptoms as described according to New York Heart Association class IV, the amount of at least one biomarker selected from the group consisting of cholesterylester C18:1 and cholesterylester C18:2, wherein the sample is a plasma or serum sample;

b) pre-treating the sample using an extraction step prior to detecting the amount of the at least one biomarker c) comparing the amount of said at least one biomarker to a reference, whereby heart failure is to be diagnosed i) if the amount of said at least one biomarker is significantly decreased as compared to the reference when the reference is derived from a subject or group of subjects known not to suffer from heart failure or is a calculated reference; or ii) if the amount of said at least one biomarker is essentially identical to the reference when the reference is derived from a subject or group of subjects known to suffer from heart failure.

2. The method of claim 1, wherein the heart failure is heart failure according to New York Heart Association class I.

3. The method of claim 2, further comprising detecting at least one additional biomarker, wherein the at least one additional biomarker is selected from Table 4a to c or 6.

4. The method of claim 1, wherein the sample of the subject has been obtained under resting.

5. The method of claim 4, further comprising detecting at least one additional biomarker, wherein the at least one additional biomarker is selected from Table 1 a to c or 4a to c.

6. The method of claim 1, wherein the heart failure is congestive heart failure.

7. The method of claim 1, wherein the subject suffers from dilated cardiomyopathy, ischemic cardiomyopathy, and/or hypertrophic cardiomyopathy.

8. A method for identifying whether a subject is in need for a therapy of heart failure comprising the steps of the method of claim 1, and a further step of identifying a subject in need for therapy if heart failure is diagnosed.

9. The method of claim 1, further comprising detecting at least one additional biomarker, wherein the at least one additional biomarker is selected from Table 1a to c, 3, 4a to c, or 6.

10. The method of claim 1, wherein mass spectrometry is used for detecting the amount of the at least one biomarker.

11. The method of claim 10, wherein the mass spectrometry comprises LC-MS, LC-MS/MS, GC-MS, or SPE-LC-MS/MS.

12. A method of treating a subject diagnosed with heart failure comprising:
a. providing a diagnosis of heart failure for a subject according to the method of claim 1 and
b. providing one or more treatments for the subject wherein the one or more treatments is the administration of one or more medications.

13. The method of claim 12, wherein the one or more medications are selected from the group consisting of: ACE inhibitors, Beta Blockers, AT-1 inhibitors, Aldosteron Antagonists, Renin Antagonists, Diuretics, Ca-Sensitizer, Digitalis Glykosides, polypeptides of the protein S100 family, and natriuretic peptides BNP and/or ANP.

14. A method for determining whether a therapy against heart failure is successful in a subject receiving heart failure therapy comprising the steps of:
a) detecting in a sample of a subject suspected to suffer from heart failure and who is recieving one or more heart failure therapies the amount of at least one biomarker selected from the group consisting of cholesterylester C18:1 and cholesterylester C18:2, wherein the sample is a plasma or serum sample;
b) comparing the amount of said at least one biomarker to a reference,
whereby heart failure is to be diagnosed
  i) if the amount of said at least one biomarker is significantly decreased as compared to the reference when the reference is derived from a subject or group of subjects known not to suffer from heart failure or is a calculated reference; or
  ii) if the amount of said at least one biomarker is essentially identical to the reference when the reference is derived from a subject or group of subjects known to suffer from heart failure;
c) determining that a therapy is successful if no heart failure is diagnosed.

* * * * *